US008241905B2

(12) United States Patent
Forgacs et al.

(10) Patent No.: US 8,241,905 B2
(45) Date of Patent: Aug. 14, 2012

(54) SELF-ASSEMBLING CELL AGGREGATES AND METHODS OF MAKING ENGINEERED TISSUE USING THE SAME

(75) Inventors: Gabor Forgacs, Columbia, MO (US); Karoly Jakab, Columbia, MO (US); Adrian Neagu, Columbia, MO (US); Vladimir Mironov, Mount Pleasant, SC (US)

(73) Assignees: The Curators of the University of Missouri, Columbia, MO (US); MUSC Foundation for Research Development, Charleston, SC (US)

( * ) Notice: Subject to any disclaimer, the term of this patent is extended or adjusted under 35 U.S.C. 154(b) by 1111 days.

(21) Appl. No.: 10/590,446

(22) PCT Filed: Feb. 24, 2005

(86) PCT No.: PCT/US2005/005735
§ 371 (c)(1),
(2), (4) Date: Oct. 10, 2007

(87) PCT Pub. No.: WO2005/081970
PCT Pub. Date: Sep. 9, 2005

(65) Prior Publication Data
US 2008/0070304 A1    Mar. 20, 2008

Related U.S. Application Data

(60) Provisional application No. 60/547,161, filed on Feb. 24, 2004.

(51) Int. Cl.
*C12N 5/02* (2006.01)
*C12N 5/07* (2010.01)
(52) U.S. Cl. .................................. 435/395; 435/397
(58) Field of Classification Search ............... 435/395, 435/397
See application file for complete search history.

(56) References Cited

U.S. PATENT DOCUMENTS

| | | | |
|---|---|---|---|
| 6,979,670 | B1 | 12/2005 | Lyngstadaas et al. |
| 2002/0182633 | A1* | 12/2002 | Chen et al. ............... 435/7.1 |
| 2003/0153078 | A1* | 8/2003 | Libera et al. ............. 435/383 |
| 2004/0219133 | A1 | 11/2004 | Lyles |
| 2004/0237822 | A1* | 12/2004 | Boland et al. ............. 101/483 |
| 2004/0253365 | A1 | 12/2004 | Warren et al. |
| 2005/0276791 | A1 | 12/2005 | Hansford et al. |
| 2007/0142916 | A1 | 6/2007 | Olson, Jr. et al. |
| 2007/0231787 | A1 | 10/2007 | Voelker |
| 2009/0248145 | A1 | 10/2009 | Chan et al. |

FOREIGN PATENT DOCUMENTS

EP 2 090 584 A1 8/2009

OTHER PUBLICATIONS

Koibuchi et al.1999. Behavior of cells in artificially made cell aggregates and tissue fragments after grafting to developing hind limb buds in *Xenopus laevis*, International Journal of Developmental Biology, vol. 43, pp. 141-148.*

Nickerson, et al., 2001. Three-Dimensional Tissue Assemblies: Novel Models for the Study of *Salmonella enterica* Serovar Typhimurium Pathogenesis. Infection and Immunity, vol. 69, No. 11, pp. 7106-7120.*

Yamauchi, et al. 2003. A Three-dimensional Cell Culture Model for Bovine Endometrium: Regeneration of a Multicellular Spheroid Using Ascorbate. Placenta, vol. 24, pp. 258-269.*

Furukawa et al. 2001.Tissue-engineered skin using aggregates of normal human skin fibroblasts and biodegradable material J Artif. Organs, vol. 4, pp. 353-356.*

Mizumoto et al.1999. Formation of cylindrical multicellular aggregate (cylindroid) and expression of liver specific functions of primary rat hepatocytes. Cytotechnology, vol. 31, pp. 69-75.*

Tang et al. 2003. Molding of Three-Dimensional Microstructures of Gels. Journal of American Chemical Society (i.e., J. Am. Chem. Soc.),vol. 125, No. 43, pp. 12988-12989.*

Kelm, J. M., et al., "Microscale Tissue Engineering Using Gravity-Enforced Cell Assembly," Trends in Biotechnology, Apr. 2004, pp. 195-202, vol. 22, No. 4.

Ryan et al., "Tissue spreading on implantable substrates is a competitive outcome of cell-cell vs. cell-substratum adhesivity", Proceedings of the National Academy of Sciences, 98(8):4323-4327 (Apr. 10, 2001).

Mombach et al., "Quantitative comparison between differential adhesion models and cell sorting in the presence and absence of fluctuations", Physical Review Letters, 75(11):2244-2247 (Sep. 11, 1995).

Constans, "Body by Science", The Scientist, 17(19):34, available web site http://www.the-scientist.com/article/display/14154/, 7 pages, (2003).

Glazier et al., "Simulation of the differential adhesion driven rearrangement of biological cells", Physical Review E, 47(3):2128-2154 (Mar. 1993), The American Physical Society.

Stiles, "UA Wins R & D 100 Award for Machine that Prints Tissue Cell-By-Cell", UANews, Dec. 2, 2003, 2 pages, http://uanews.org/cgi-bin/WebObjects/UANews.woa/wa/goPrint?ArticleID=8305, accessed Feb. 1, 2005, 2 pages.

"Sciperio, Inc. 2003 R&D 100 Award Winner", Sciperio, http://www.sciperio.com/news/20031016.asp, accessed Feb. 1, 2005, 2 pages.

(Continued)

*Primary Examiner* — Jon P Weber
*Assistant Examiner* — Kailash C Srivastava
(74) *Attorney, Agent, or Firm* — Senniger Powers LLP

(57) ABSTRACT

A composition comprising a plurality of cell aggregates for use in the production of engineered organotypic tissue by organ printing. A method of making a plurality of cell aggregates comprises centrifuging a cell suspension to form a pellet, extruding the pellet through an orifice, and cutting the extruded pellet into pieces. Apparatus for making cell aggregates comprises an extrusion system and a cutting system. In a method of organ printing, a plurality of cell aggregates are embedded in a polymeric or gel matrix and allowed to fuse to form a desired three-dimensional tissue structure. An intermediate product comprises at least one layer of matrix and a plurality of cell aggregates embedded therein in a predetermined pattern. Modeling methods predict the structural evolution of fusing cell aggregates for combinations of cell type, matrix, and embedding patterns to enable selection of organ printing processes parameters for use in producing an engineered tissue having a desired three-dimensional structure.

35 Claims, 16 Drawing Sheets

OTHER PUBLICATIONS

Graner et al., "Simulation of Biological Cell Sorting using a Two-Dimensional Extended Potts Model", Physical Review Letters, 69(13):2013-2016 (Sep. 28, 1992), The American Physical Society.

Mironov et al., "Organ printing: self-assembling cell aggregates as 'BIOINK'", Science & Medicine, 9(2):69-71 (Apr. 2003).

Mironov et al., "Organ printing: computer-aided jet-based 3D tissue engineering", Trends in Biotechnology, 21(4):157-161 (Apr. 2003).

Martin et al., "Computer-Based Technigue for Cell Aggregation Analysis and Cell Aggregation in In Vitro Chondrogenesis", Cytometry, 28(2):141-146 (1997) John Wiley & Sons, Inc.

Koibuchi et al., "Behavior of cells in artificially made cell aggregates and tissue fragments after grafting to developing hind limb buds in *Xenopus laevis*", The International Journal of Developmental Biology, 43(2):141-148 (1999) University of the Basque Country Press, Spain.

Steinberg "Does differential adhesion govern self-assembly processes in histogenesis? Equilibrium configurations and the emergence of a hierarchy among populations of embryonic cells" The Journal of Experimental Zoology, 173(4):395-433 (Apr. 1970).

Steinberg et al., "Liquid behavior of embryonic tissues", Cell Behaviour, Cambridge University Press (Editors R. Bellairs, A.S.G. Curtis and G. Dunn) pp. 583-697 (1982).

Timmins et al., "Hanging-drop Multicellular Spheroids as a Model of Tumour Angiogenesis" Angiogenesis, 7(2):97-103 (2004).

Dai et al., "Fibroblast Aggregation by Suspension with Conjugates of Poly(ethylene glycol) and RGD" Biotechnology and Bioengineering 50(4):349-356 (1996).

Foty et al., "Surface tensions of embryonic tissues predict their mutual envelopment behavior", Development, 122(5):1611-1620 (1996).

Forgacs et al., "Viscoelastic Properties of Living Embryonic Tissues: a Quantitative Study" Biophysical Journal, 74(5):2227-2234 (May 1998).

Furukawa et al., "Formation of Human Fibroblast Aggregates (Spheroids) by Rotational Culture" Cell Transplantation, 10(4-5):441-445 (2001).

Glicklis et al., "Modeling Mass Transfer in Hepatocyte Spheroids via Cell Viability, Spheroid Size, and Hepatocellular Functions" Biotechnology and Bioengineering, 86(6):672-680 (Jun. 2004).

Korff et al., "Blood vessel maturation in a 3-dimensional spheroidal coculture model: direct contact with smooth muscle cells regulates endothelial cell quiescence and abrogates VEGF responsiveness", The FASEB Journal, 15:447-457 (Feb. 2001).

Foty et al., "The Differential Adhesion Hypothesis: a Direct Evaluation", Developmental Biology, 278(1):255-263 (Feb. 2005).

International Search Report for PCT/US05/05735 mailed Dec. 7, 2007, 1 page.

Tsang, V. L., et al., "Three-Dimensional Tissue Fabrication," Advanced Drug Delivery Reviews, 2004, pp. 1635-1647, vol. 56.

International Search Report, PCT/US2011/023520, dated Oct. 31, 2011, 5 pages.

\* cited by examiner

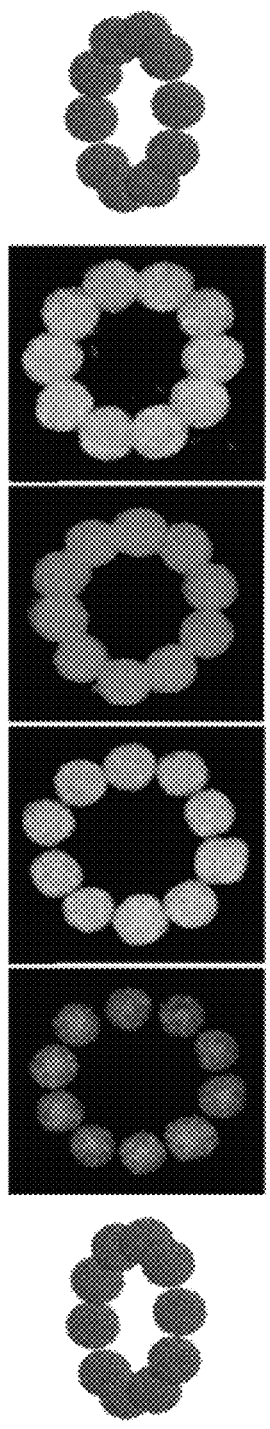
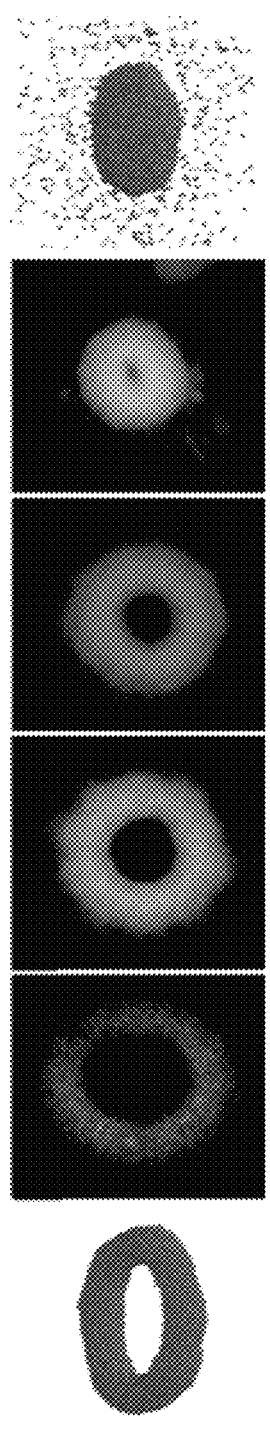
FIG. 8A FIG. 8C FIG. 8E FIG. 8G FIG. 8I FIG. 8K
FIG. 8B FIG. 8D FIG. 8F FIG. 8H FIG. 8J FIG. 8L

SELF-ASSEMBLING CELL AGGREGATES AND METHODS OF MAKING ENGINEERED TISSUE USING THE SAME

FIELD OF THE INVENTION

The present invention relates generally to the field of tissue engineering and more particularly to production of engineered tissues having desired structures.

BACKGROUND

Tissue engineering provides promising solutions to problems caused by the growing demand for organ/tissue replacement therapies coupled with a chronically low supply of transplantable organs. In the United States, for example, thousands of people are on the national waiting list for organ transplants. Many will likely perish for lack of suitable organ replacements. To lessen and eventually solve the problem of inadequate supply of organs for transplantation, tissue engineers need to be able to build and grow transplantable organs or organ substitutes in a laboratory, with high precision, on large scale, and in a relatively short amount of time.

A variety of methods and devices for tissue engineering have been attempted and developed with limited success. There has been some success, for example, with production of non-vascularized tissues (e.g., cartilage and tendons). However, assembly of vascularized three-dimensional soft organs has not been accomplished.

One of the more promising tissue engineering technologies that is emerging is organ printing. Organ printing is generally a computer-aided, dispenser-based, three-dimensional tissue-engineering technology aimed at constructing functional organ modules and eventually entire organs layer-by-layer. Organ printing technology, prior to the present invention, has been based on seeding individual cells into biodegradable polymer scaffolds or gels, similar to traditional tissue engineering approaches, but using a dispensing apparatus that employs, for example, a technology analogous to an ink-jet printer or more complex three-dimensional rapid prototype printers (which partially explains the origin of the phrase "organ printing"). Once implanted in the scaffold, the embedded cells are cultured in a bioreactor for several weeks during which time the cell population expands. The resulting tissue may be implanted into a patient where the maturation of the new organ may or may not take place.

Organ printing based on deposition of single cells in a scaffold has many of the same shortcomings as traditional tissue engineering. First, it has not yet achieved production of tissues that require provision of a vascular network, which limits the size and type of the tissue that can be produced. It is also difficult to control the structure of the tissue as it grows from the seeds. Thus, tissue having the desired shape and required stability for a target organ cannot be produced reliably. Further, the individually seeded cells may not survive long enough to sufficiently proliferate. After the cells have been seeded in a scaffold a relatively long incubation period is also required to allow the cells enough time to multiply and form a significant amount of tissue.

Therefore, what is needed is a new and improved technology that enables rapid, reliable, and precise building of target organs. What is further needed is a method, combined with appropriate devices, capable of producing mechanically stable and long-lived three-dimensional organotypic tissue structures.

SUMMARY OF THE INVENTION

In one embodiment, the present invention provides a method of producing a plurality of fused aggregates forming a desired three-dimensional structure. The method comprises depositing a layer of a matrix on a substrate; embedding a plurality of cell aggregates, each comprising a plurality of cells, in the layer of the matrix, the aggregates being arranged in a predetermined pattern; allowing at least one aggregate of said plurality of cell aggregates to fuse with at least one other aggregate of the plurality of cell aggregates to form the desired structure; and separating the structure from the matrix.

Also provided is a computerized method of producing a plurality of fused aggregates forming a desired three-dimensional structure. The method comprises selecting an embedding pattern by which a plurality of cell aggregates are to be embedded in a matrix, the plurality of cell aggregates each comprising a plurality of cells; establishing a group of candidate matrices to be evaluated for use as the matrix based at least in part on the compatibility of the candidate matrices with the cell aggregates; executing a computer simulation based on parameters comprising an interaction force between two of the cells of each of the plurality of cells, an interaction force between one of the cells and each of the candidate matrices, and an interaction force between two volume elements of each of the candidate matrices to predict structural evolutions of the pluralities of cells that are likely to occur if said plurality of cell aggregates are embedded in each of the candidate matrices in accordance with the embedding pattern; and selecting one of the candidate matrices that is predicted to result in the cell aggregates evolving into the desired three-dimensional structure for use in producing fused aggregates forming the desired structure.

Also provided is a computerized method of producing a plurality of fused aggregates forming a desired three-dimensional structure. The method comprises identifying a matrix to be used to temporarily support a plurality of cell aggregates embedded therein in accordance with a predetermined embedding pattern, the cell aggregates each comprising a plurality of cells; establishing a group of candidate cell types to be evaluated for use as a constituent of at least one of the plurality of cell aggregates based at least in part on the suitability of cells of the candidate cell types to perform a desired biological function; executing a computer simulation based on parameters comprising interaction forces between two cells of the same type for each of the candidate cell types, an interaction force between one of the cells of each candidate cell type and the matrix, and an interaction force between two volume elements of the matrix to predict structural evolutions of the pluralities of cells that are likely to occur for each cell type if said plurality of cell aggregates comprising cells of the respective candidate cell type are embedded in the matrix in accordance with the embedding pattern; and selecting one of the candidate cell types that is predicted to result in the cell aggregates evolving into the desired three-dimensional structure for use in producing fused aggregates forming the desired structure.

Also provided is a computerized method of producing a plurality of fused aggregates forming a desired three-dimensional structure. The method comprises identifying a matrix to be used to temporarily support a plurality of cell aggregates embedded therein in accordance with an embedding pattern, the cell aggregates each comprising a plurality of cells; establishing a group of candidate embedding patterns to be evaluated for use as the embedding pattern by which said plurality of cell aggregates are to be embedded in the matrix based at least in part on similarity of the embedding pattern to the desired three-dimensional structure; executing a computer simulation based on parameters comprising interaction forces between two of the cells, an interaction force between one of the cells and the matrix, and an interaction force between two volume elements of the matrix to predict structural evolutions of the pluralities of cells that are likely to occur for each of the candidate embedding patterns if said plurality of cell are embedded in the matrix in accordance with the respective embedding pattern; and selecting one of the candidate embedding patterns that is predicted to result in the cell aggregates evolving into the desired three-dimensional structure for use in producing fused aggregates forming the desired structure.

In another embodiment, the present invention provides a composition comprising a plurality of cell aggregates, wherein each cell aggregate comprises a plurality of living cells, and wherein the cell aggregates are substantially uniform in size and/or shape.

The present invention also provides a method of preparing a plurality of cell aggregates. The method comprises preparing a cell suspension comprising a plurality of living cells; centrifuging the cell suspension to form a cellular material comprising at least some of the plurality of living cells; extruding the cellular material through an orifice; and forming the extruded cellular material into cell aggregates of substantially uniform size or shape.

Also provided is an apparatus for producing a plurality of substantially uniform cell aggregates. The apparatus comprises an extrusion system adapted to receive a container holding a pellet comprising a plurality of cells and to extrude the pellet through an orifice; and a cutting system operable to cut the extrudate into a plurality of pieces as the extrudate is being extruded through the orifice.

The present invention also provides a three-dimensional layered structure. The structure comprises at least one layer of a biocompatible matrix; and a plurality of cell aggregates, each cell aggregate comprising a plurality of living cells; wherein the cell aggregates are embedded in the at least one layer of biocompatible matrix in a predetermined pattern.

BRIEF DESCRIPTION OF THE DRAWINGS

FIGS. 8A-8L show initial and final cell aggregate configurations for simulations (FIGS. 8A-8B and 8K-8L) and experiments embedding CHO cell aggregates in Neurogel™ disks (FIGS. 8C-8D), and in collagen gels of concentration 1.0 mg/ml (FIGS. 8E-8F), 1.2 mg/ml (FIGS. 8G-8H), and 1.7 mg/ml (FIGS. 8I-8J), as described in Example 2;

Corresponding reference characters indicate corresponding parts throughout the drawings.

DETAILED DESCRIPTION

Figure 1:
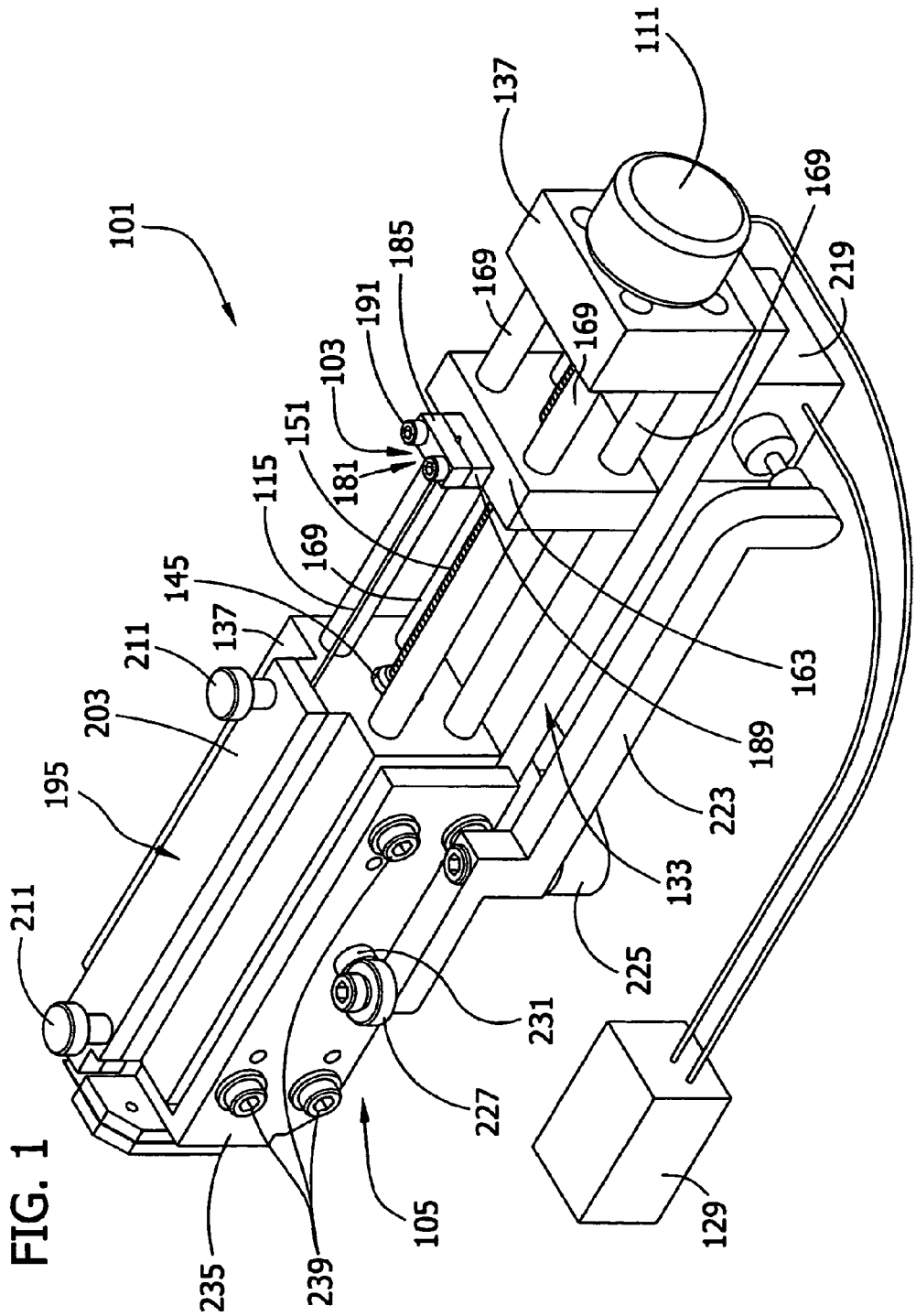
FIG. 1 is a perspective of one embodiment of apparatus for making cell aggregates of the present invention.
Figure 2:
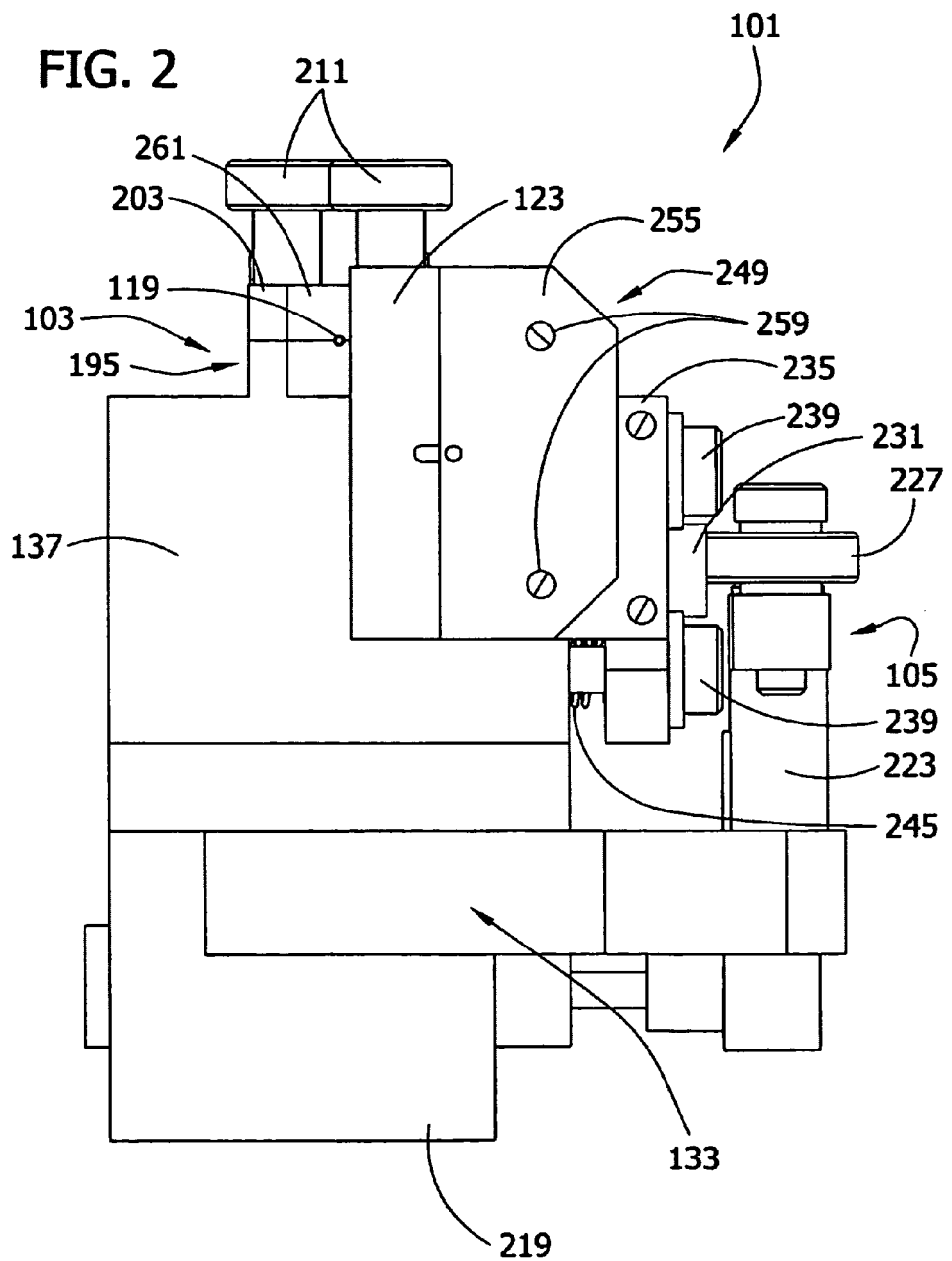
FIG. 2 is an end view of the apparatus.
Figure 3:
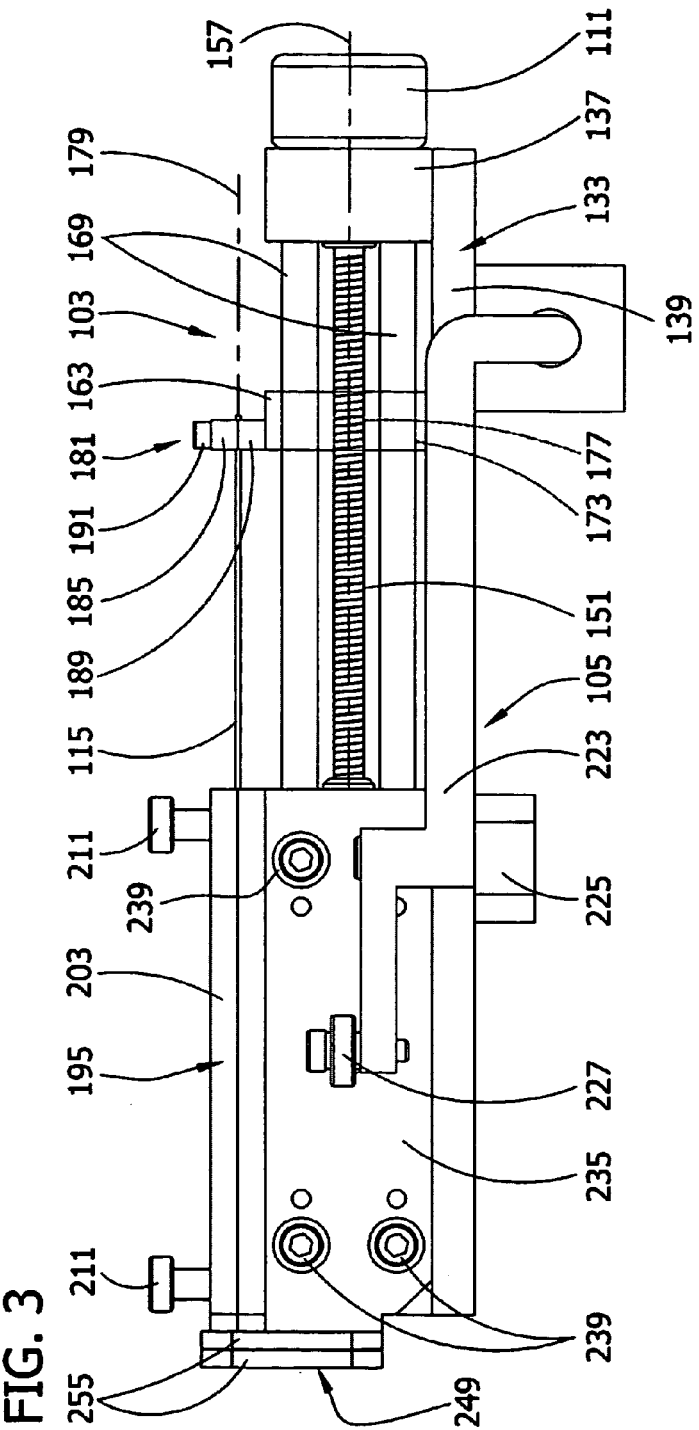
FIG. 3 is a side elevation thereof.

In contrast to previously known methods of tissue engineering which are based on seeding individual cells into biodegradable polymer scaffolds or gels, the methods of the present invention use cell aggregates as the building blocks of tissue formation. Using cell aggregates as building blocks instead of isolated cells has a number of advantages. For example, because cell aggregates may be composed of hundreds to thousands of cells (i.e., they are essentially a prefabricated piece of tissue), cell aggregates provide critical cell concentrations, which may be difficult to achieve by other methods, and can significantly reduce the time required to "print" the desired structure or tissue. Furthermore, the mechanical hardship involved in the dispensing process (e.g., in the ink-jet technology to print individual cells) is less damaging to cell aggregates, which contain a multitude of cells, than it is for individual cells which may be damaged or killed during the dispensing process. In addition, because cell aggregates are already three-dimensional tissue fragments, they are more amenable to fusing to form a three-dimensional structure, than are single cells. Finally, because cell aggregates may contain several cell types and a pre-built internal structure, considerable time can be saved during post-process tissue and organ maturation.

One process of making an engineered tissue having a desired structure (e.g., an organotypic tissue) using the inventive methods and materials described herein involves use of a composition (sometimes referred to as "bio-ink") comprising a plurality of cell aggregates (sometimes referred to as "bio-ink particles"). A target tissue structure blueprint (e.g., a series of images showing the target tissue structure (e.g., organ) in thin sections which may be reconstituted, for example by a computer, into a three-dimensional representation of the tissue structure) is also acquired. The blueprint may be obtained, for example, by MRI. Then a dispensing unit under the guidance of a computer control unit embeds the cell aggregates into a matrix (e.g., a bio-degradable polymeric or gel scaffold) according to a geometric pattern that is designed to result in the cell aggregates evolving into a structure representative of the target organ. The cell aggregates reside in the matrix where they fuse together and evolve into an organotypic tissue structure. The tissue structure is separated from the matrix (e.g., by exposing the matrix to a stimulus that degrades the matrix). Then the engineered tissue is placed in a bio-reactor/maturation unit for accelerated maturation and post-processing support.

The present invention recognizes that cell aggregates (e.g., bio-ink particles) have the ability to fuse into three-dimensional organotypic structures upon deposition into a stimuli-sensitive matrix made of biodegradable polymers or gels. The ability of cell aggregates to fuse is based on the concept of tissue fluidity, according to which embryonic tissues (or more generally, tissues composed of adhesive and motile cells) in many respects can be considered as liquids. In particular, in suspension or on non-adhesive surfaces, various multicellular aggregates (comprising adhesive and motile cells) round up into spherical shape similarly to liquid droplets. Thus, closely-spaced (e.g., within about 0.5 aggregate diameters) or contiguously-placed aggregates embedded in a matrix formed from appropriately chosen gels or polymers can fuse to form tissue constructs having a desired geometry. Moreover, the principles of the Differential Adhesion Hypothesis (M. S. Steinberg, "Does differential adhesion govern self-assembly processes in histogenesis? Equilibrium configurations and the emergence of a hierarchy among populations of embryonic cells", *J Exp Zool* 173, p. 395-433 (1970); M. S. Steinberg and T. J. Poole, "Liquid behavior of embryonic tissues", in *Cell Behavior*, pp. 583-697, (eds. Bellairs, R., Curtis, A. S. G. & Dunn, G.) Cambridge University Press (1982)) have been determined to predictably describe evolution of the structure formed by constituent cells of fusing cell aggregates.

Having provided a general overview of one embodiment of a process of producing tissue, systems, processes and materials used therein will now be described in more detail.

Bio-Ink

The present invention thus provides compositions comprising cell aggregates (i.e., "bio-ink" or "bio-ink compositions") for use in the methods described herein. These compositions comprise a plurality of cell aggregates, wherein each cell aggregate comprises a plurality of living cells, and wherein the cell aggregates are substantially uniform in size and/or shape. The cell aggregates are characterized by the capacity: 1) to be delivered by computer-aided automatic cell dispenser-based deposition or "printing," and 2) to fuse into, or consolidate to form, self-assembled histological constructs.

In contrast to cell aggregates produced by previously known methods that may vary in both size and shape, the bio-ink of the present invention comprises a plurality of cell aggregates that have a narrow size and shape distribution (i.e., are substantially uniform in size and/or shape). The uniformity of the cell aggregates in the bio-ink is particularly advantageous when the bio-ink used in the methods described herein, since the uniformity of shape and/or size of the cell aggregates provides for greater ease in printing and more predictability in aggregate fusion.

Thus, in one embodiment, the bio-ink comprises a plurality of cell aggregates, wherein the cell aggregates are substantially uniform in shape. By "substantially uniform in shape" it is meant that the spread in uniformity of the aggregates is not more than about 10%. In another embodiment, the spread in uniformity of the aggregates is not more than about 5%.

The cell aggregates used herein can be of various shapes, such as, for example, a sphere, a cylinder (preferably with equal height and diameter), rod-like, or cuboidal (i.e., cubes), among others. Although other shaped aggregates may be used, it is generally preferable that the cell aggregates be spherical, cylindrical (with equal height and diameter), or cuboidal (i.e., cubes), as aggregates of these shapes tend to cause less clogging of the dispensers during printing.

For example, in one embodiment, the bio-ink comprises a plurality of aggregates wherein the aggregates are substantially spherical. By "substantially spherical" it is meant that the principle radii of curvature of the cell aggregate are substantially equal at all points on the surface of the aggregate (i.e., vary by about 10% or less over all points on the surface of the aggregate). In a preferred embodiment, the principle radii of curvature of the cell aggregate vary by about 5% or less over all points on the surface of the aggregate. In contrast, previously known examples of cell aggregates are typically non-uniform spheroidal cell aggregates. By "spheroidal cell aggregates" it is meant that while the aggregate is generally shaped like a sphere, the radii of curvature of the aggregate are not substantially equal for all points on the surface of the aggregate (i.e., vary by substantially more than 10% over all points on the surface of the aggregate).

Although the exact number of cells per aggregate is not critical, it will be recognized by those skilled in the art that the size of each aggregate (and thus the number of cells per aggregate) is limited by the capacity of nutrients to diffuse to the central cells, and that this number may vary depending on cell type. Cell aggregates may comprise a minimal number of cells (e.g., two or three cells) per aggregate, or may comprise many hundreds or thousands of cells per aggregate. Typically, cell aggregates comprise hundreds to thousands of cells per aggregate. For purposes of the present invention, the cell aggregates are typically from about 100 microns to about 600 microns in size, although the size may be greater or less than this range, depending on cell type. In one embodiment, the cell aggregates are from about 250 microns to about 400 microns in size. In another embodiment, the cell aggregates are about 250 microns in size. For example, spherical cell aggregates are preferably from about 100 microns to about 600 microns in diameter, cylindrical cell aggregates are preferably from about 100 microns to about 600 microns in diameter and height, and the sides of cuboidal cell aggregates are preferably from about 100 microns to about 600 microns in length. Aggregates of other shapes will typically be of similar size.

Although the size of the cell aggregates may vary, it is preferable that the size of the aggregates present in a particular bio-ink composition be substantially uniform. Compositions comprising aggregates of substantially uniform size are generally more amenable for deposition of the aggregates using automated depositing devices. For instance, if the cell aggregates differ in size, it will be difficult to reliably deposit a single cell aggregate at a desired position in the matrix. By "substantially uniform in size" it is meant that the aggregates' size distribution has a spread not larger than about 10%. In one embodiment, the aggregates' size distribution has a spread not larger than about 5%.

Preferably, the bio-ink comprises cell aggregates that are both substantially uniform in size and substantially uniform in shape.

Many cell types may be used to form the bio-ink cell aggregates. In general, the choice of cell type will vary depending on the type of three-dimensional construct to be printed. For example, if the bio-ink particles are to be used to print a blood vessel type three dimensional structure, the cell aggregates will advantageously comprise a cell type or types typically found in vascular tissue (e.g., endothelial cells, smooth muscle cells, etc.). In contrast, the composition of the cell aggregates may vary if a different type of construct is to be printed (e.g., intestine, liver, kidney, etc.). One skilled in the art will thus readily be able to choose an appropriate cell type(s) for the aggregates, based on the type of three-dimensional construct to be printed. Non-limiting examples of suitable cell types include contractile or muscle cells (e.g., striated muscle cells and smooth muscle cells), neural cells, connective tissue (including bone, cartilage, cells differentiating into bone forming cells and chondrocytes, and lymph tissues), parenchymal cells, epithelial cells (including endothelial cells that form linings in cavities and vessels or channels, exocrine secretory epithelial cells, epithelial absorptive cells, keratinizing epithelial cells, and extracellular matrix secretion cells), and undifferentiated cells (such as embryonic cells, stem cells, and other precursor cells), among others.

The bio-ink particles may be homocellular aggregates (i.e., "monocolor bio-ink") or heterocellular aggregates (i.e., "multicolor bio-ink"). "Monocolor bio-ink" comprises a plurality of cell aggregates, wherein each cell aggregate comprises a plurality of living cells of a single cell type. In contrast, "multicolor bio-ink" comprises a plurality of cell aggregates, wherein each individual cell aggregate comprises a plurality of living cells of at least two cell types, or at least one cell type and extracellular matrix (ECM) material, as discussed below.

When a single aggregate comprises more than one cell type (i.e., heterocellular aggregate or "multicolor bio-ink"), the cells within the aggregate may "sort out" to form a particular internal structure for the aggregate. The pattern evolution in sorting out is consistent with the predictions of the Differential Adhesion Hypothesis (DAH), discussed in more detail herein. The DAH explains the liquid-like behavior of cell populations in terms of tissue surface and interfacial tensions generated by adhesive and cohesive interactions between the component cells. In general, cells will sort out based on differences in the adhesive strength of the cells. For example, cell types that sort to the center of a heterocellular aggregate generally have a stronger adhesion strength (and thus higher surface tension) than cells that sort to the outside of the aggregate.

Furthermore, when a heterocellular aggregate is composed of cells of tissues that are neighbors in normal development, in the course of sorting they may recover their physiological conformation. Thus, heterocellular aggregates may comprise a sort of pre-built internal structure, based on the adhesive and cohesive properties of the component cells, and the environment in which the cells are located. This can be used to build more complex biological structures. For example, while building a simple contractile tube, monocolor bioink composed of muscle cells can be used; to build a blood vessel-like structure, at least two cell types (i.e., endothelial cells and smooth muscle cells) can be used. By printing bio-ink particles composed of these two cell types randomly dispersed in the aggregate, in the course of postprinting structure formation, these cell types sort and with the right choice of the scaffold, endothelial cells will line the internal structure of the tube (i.e., lumen), whereas smooth muscle cells will form the outer layer of the tube. The optimal structure can be achieved by varying the composition of the aggregate (e.g., ratio of endothelial to smooth muscle cells), by the size of the aggregate and the composition of the scaffold (e.g., possibly different scaffold material used in the interior and exterior of the printed construct).

In addition to one or more cell types, the bio-ink aggregates can further be fabricated to contain extracellular matrix (ECM) material in desired amounts. For example, the aggregates may contain various ECM proteins (e.g., collagen, fibronectin, laminin, elastin, and/or proteoglycans). Such ECM material can be naturally secreted by the cells, or alternately, the cells can be genetically manipulated by any suitable method known in the art to vary the expression level of ECM material and/or cell adhesion molecules, such as selectins, integrins, immunoglobulins, and cadherins, among others. In another embodiment, either natural ECM material or any synthetic component that imitates ECM material can be incorporated into the aggregates during aggregate formation, as described below.

The bio-ink cell aggregates can be suspended in any physiologically acceptable medium, typically chosen according to the cell type(s) involved. The tissue culture media may comprise, for example, basic nutrients such as sugars and amino acids, growth factors, antibiotics (to minimize contamination), etc.

Bio-ink particles described herein can be used in accordance with the methods of the present invention to produce three-dimensional fused tissue constructs. The bio-ink can be dispensed using any of a variety of printing or dispensing devices, such as those discussed below. Therefore, it is advantageous to store the bio-ink compositions in the storage chamber of a container, such as a printer cartridge, that is compatible with a printing or dispensing device. Thus, in one embodiment, the present invention provides a printer cartridge comprising a storage chamber, wherein the bio-ink is stored in the storage chamber. Because the aggregates of the bio-ink may begin to fuse together before printing if allowed to sit for long periods of time, it is generally preferable to transfer the bio-ink to the printer cartridge within 2 hours, more preferably within 1 hour, and even more preferably within 30 minutes of printing to avoid any fusion of aggregates in the bio-ink before printing.

Method of Making Bio-Ink Particles

A variety of methods of making cell aggregates are known in the art such as, for example, the "hanging drop" method wherein cells in an inverted drop of tissue culture medium precipitate and aggregate; shaking cell suspensions in a laboratory flask; and various modifications of these techniques. See, e.g., N. E. Timmins, et al., Angiogenesis 7, 97-103 (2004); W. Dai, et al., Biotechnology and Bioengineering 50, 349-356 (1996); R. A. Foty, et al., *Development* 122, 1611-1620 (1996); G. Forgacs, et al., *Biophys. J.* 74, 2227-2234 (1998); K. S. Furukawa, et al., *Cell Transplantation* 10, 441-445 (2001); R. Glicklis, et al., Biotechnology and Bioengineering 86, 672-680 (2004); and T. Korff, et al., *FASEB J.* 15, 447-457 (2001). Although such methods can be used to produce cell aggregates, the aggregates produced by these methods are typically not substantially uniform in size and/or shape.

The present invention addresses this problem by providing a method capable of reproducibly producing cell aggregates that are substantially uniform in size and shape. Therefore, in one embodiment, the present invention is directed to a method of preparing a plurality of cell aggregates, the method comprising: preparing a cell suspension comprising a plurality of live cells; centrifuging the cell suspension to form a firm cellular material (e.g., a pellet) comprising at least some of the plurality of live cells; transferring the firm cellular material to a container (e.g., a micropipette), the container having an orifice; extruding the cellular material through the orifice; and forming (e.g., by slicing or cutting) the extruded cellular material into cell aggregates of substantially uniform size and shape as the extruded cellular material exits the orifice.

As discussed above, a large variety of cell types may be used to form the bio-ink of the present invention. For example, the cell suspension may comprise only one cell type (i.e., when monocolor bio-ink is being prepared), or alternately, may comprise two or more cell types (i.e., when multicolor bio-ink is being prepared). Furthermore, the cell suspension may comprise extracellular matrix-like gel.

Once a cell suspension comprising the desired cell type(s) is chosen, the cell suspension can be centrifuged to form a pellet of cellular material. Although the duration and speed of centrifugation is not critical, centrifugation should generally occur for a period of time and at a speed sufficient so that at least some of the plurality of live cells in the suspension form a relatively firm pellet. Preferably, the pellet is sufficiently firm so that it can be transferred to a container, as described below.

After centrifugation, the cellular material collected in the pellet can be transferred to a container having an orifice, such as a tube, micropipette, or any other suitable container, by any suitable means including, for example, aspiration. The orifice of the container preferably has a size and shape similar to the desired size and shape of the cell aggregate being produced. For example, if spherical or cylindrical aggregates are being produced, the orifice preferably is circular, and has a diameter equal to the desired diameter of the cell aggregate. If the aggregate is cuboidal, the orifice is square shaped and has a side length equal to the desired length of the linear side of the cube. Thus, in a preferred embodiment, when the aggregate is to be spherical or cylindrical, the orifice is circular, and has a diameter of from about 100 microns to about 600 microns. Containers with different shapes and dimensions may readily be selected based on the desired size and shape of the cell aggregate being produced.

Once transferred to the container, the cellular material may optionally be incubated for a period of time during which the cellular material conforms to the shape of the container. The time and temperature of incubation will vary with cell type, and may readily be determined by one skilled in the art. Optionally, ECM materials, such as those described above, may be added to the cellular material prior to transferring the cellular material to the container.

The cellular material may then be extruded through the orifice of the container, and formed into cell aggregates (e.g., by slicing or cutting the extruded cellular material) as the extruded cellular material exits the orifice. Preferably, the cellular material is sliced at regular intervals, so as to produce cell aggregates of substantially uniform size and shape. Advantageously, the cellular material is sliced at intervals about equal to the desired size of the cellular aggregate. For example, the cellular material may be sliced at a constant interval, the interval being from about 100 microns to about 600 microns. In one embodiment, if cylindrical aggregates are being produced, the orifice is circular, and the extruded cellular material is sliced in intervals corresponding to the desired height of the cylindrical cell aggregates. The extruded cellular material can then be used as bio-ink particles. In another embodiment, if spherical aggregates are being produced, the orifice is circular, and the extruded cellular material is sliced into cylinders so that the height of the cylinder is equal to its diameter. The resulting cylinders may be subjected to further short-term incubation, as discussed below, to form substantially uniform spherical aggregates.

Any method capable of accurately slicing the extruded cellular material in the desired intervals may be used herein. Preferably, the extruded cellular material is sliced using an automatic device, such as the device described below. By using such an automated device, uniformity of aggregate size and/or shape is achieved, in contrast to previously known methods of aggregate formation, and the amount of time required to prepare the aggregates is reduced.

If spherical cell aggregates are being prepared, the sliced (cylindrical) cell aggregates may be incubated in any suitable flask, and shaken to produce substantially spherical aggregates. Although the time and temperature of incubation may vary depending on cell type, the aggregates are typically incubated at 37° C. for about 1 to about 5 hours. Any suitable shaking means can be used including, for example, a gyratory shaker or a low shear stress vessel, such as the NASA-developed High Aspect Ratio Vessel. Preferably the aggregates are shaken at a speed of about 15-100 revolutions per minute (rpm). The resulting aggregates are substantially spherical.

This method advantageously produces cell aggregates that are substantially uniform in both size and shape. Once formed, cell aggregates of similar composition can be suspended in a suitable medium, as described herein, and can be used as bio-ink.

Apparatus for Making Bio-Ink Particles

Although there are various ways to make cell aggregates that are suitable for use as bio-ink particles, including by hand, without departing from the scope of this invention, it may be desirable to use an automated system that is capable of producing a large number of substantially uniform cylindrical cell aggregates (i.e., about equal in diameter and within about 10-20 microns of each other in length) at a relatively high rate. It is also desirable to minimize the number of cells that are killed when a pellet comprising a plurality of cells is cut into pieces.

Referring to FIGS. 1-7, for example, one embodiment of an automated device for producing a plurality of cell aggregates is generally designated 101. In general the device 101 comprises an extruding system 103 operable to extrude a pellet comprising a plurality of cells through an orifice 119 (FIG. 2) and a cutting system 105 operable to cut the pellet into a plurality of cell aggregates as the pellet is extruded through the orifice. The operations of the extruding system 103 and cutting system 105 are coordinated so the pellet is cut into a plurality of substantially uniform pieces as the pellet is being extruded through the orifice.

In one embodiment, shown in the drawings, the extruding apparatus 103 comprises a motor 111 that is drivingly connected to a piston 115. The motor 111 is operable to advance the piston 115 through a container 117 (FIG. 4) that contains the pellet of cells to thereby extrude the pellet through the orifice 119 at one end of the container. The cutting system 105 of the particular embodiment shown in the drawings comprises a reciprocating cutting blade 123 that is operable to cut the pellet into pieces.

The motor 111 of the illustrated embodiment is a stepper motor. Preferably, the operation of the motor 111 is controlled by an electronic control system 129 (e.g., desktop computer) in electrical communication with the motor 111. The electronic control system 129 is only schematically illustrated in the drawings. The motor 111 is preferably operable to periodically pause at intervals (e.g., regular intervals) to allow the cutting system 105 the opportunity to sever the extruded portion of the pellet from the part of the pellet that still remains in the container 117 while the pellet is stationary. For example, the control system 129 can direct the motor ill to operate at a substantially constant speed for a period (e.g., a period in the range of about 1 to about 2 seconds) and then pause for a brief period (e.g., a period of about 0.5 seconds). It is understood that other actuators (e.g., a servo motor) could be used instead of a stepper motor without departing from the scope of the invention.

The motor 111 is mounted on a frame 133. The frame 133 comprises opposing blocks 137 and a plate 139 that holds the blocks in spaced relation to one another. The motor 111 is mounted on one of the blocks 137 and drivingly connected to a threaded shaft 151. The shaft 151 passes through an opening 141 in one of the blocks 137 and extends into an opening 145 in the other of the blocks. Thus, the threaded shaft 151 spans the space between the blocks 137. The shaft 151 is rotatable about its axis 157 (e.g., rotatably mounted in the openings by one or more bearings) but restrained from translational movement with respect to the frame 133 in the direction parallel to its axis.

A drive block 163 is slideably mounted between the blocks 137 for sliding movement along the axis 157 of the threaded shaft 151. The threaded shaft 151 is received in a threaded bore 177 of a drive block 163 so that rotation of the threaded shaft drives the movement of the drive block along the axis 157 of the threaded shaft. The drive block 163 is preferably slidably mounted on one or more guide rails that span the distance between the blocks 137 and are parallel to the threaded shaft 151. As illustrated in the drawings, for example, the drive block 163 can be mounted on four parallel guide rails 169 that are received in corresponding through-holes 173 through the drive block 163 that arranged in a pattern centered on the threaded bore 177.

A piston 115 (e.g., a stainless steel wire rod) is connected to the drive block 163 so that sliding movement of the drive block drives movement of the piston (e.g., along a longitudinal axis of the piston). It will be understood that various mechanisms may be used to connect the piston to the drive block, including numerous different arrangements of gears and/or linkages. In the embodiment shown in the drawings, for example, the piston 115 is secured to the drive block 163 by a piston mount 181 on the drive block. The piston mount comprises a clamp 185 that is releasably secured (e.g., by screws or other suitable fasteners) to an anvil 189 formed on one side of the drive block 163. A piston 115 is received between the clamp 185 the anvil 189 where it is secured to the piston mount 181 (e.g., by tightening the fasteners to squeeze a piston between the clamp and the drive block). When connected to the drive block 163, the piston 115 of the illustrated embodiment is preferably oriented so a longitudinal axis 179 of the piston 115 is parallel to the threaded shaft 151. A piston alignment groove 193 (FIG. 5) is preferably formed in either or both of the opposing surfaces of the clamp 185 and the anvil 189 to facilitate mounting the piston 115 on the piston mount 181 in the desired alignment. The piston mount 181 secures a piston 115 to the drive block 163 so the piston is constrained to move substantially in unison with the drive block. Notably, the piston mount 181 of the illustrated embodiment facilitates rapid replacement of a piston with a new piston in the event a piston is damaged or if it is desired to change the diameter or other characteristics of the piston.

Figure 4:
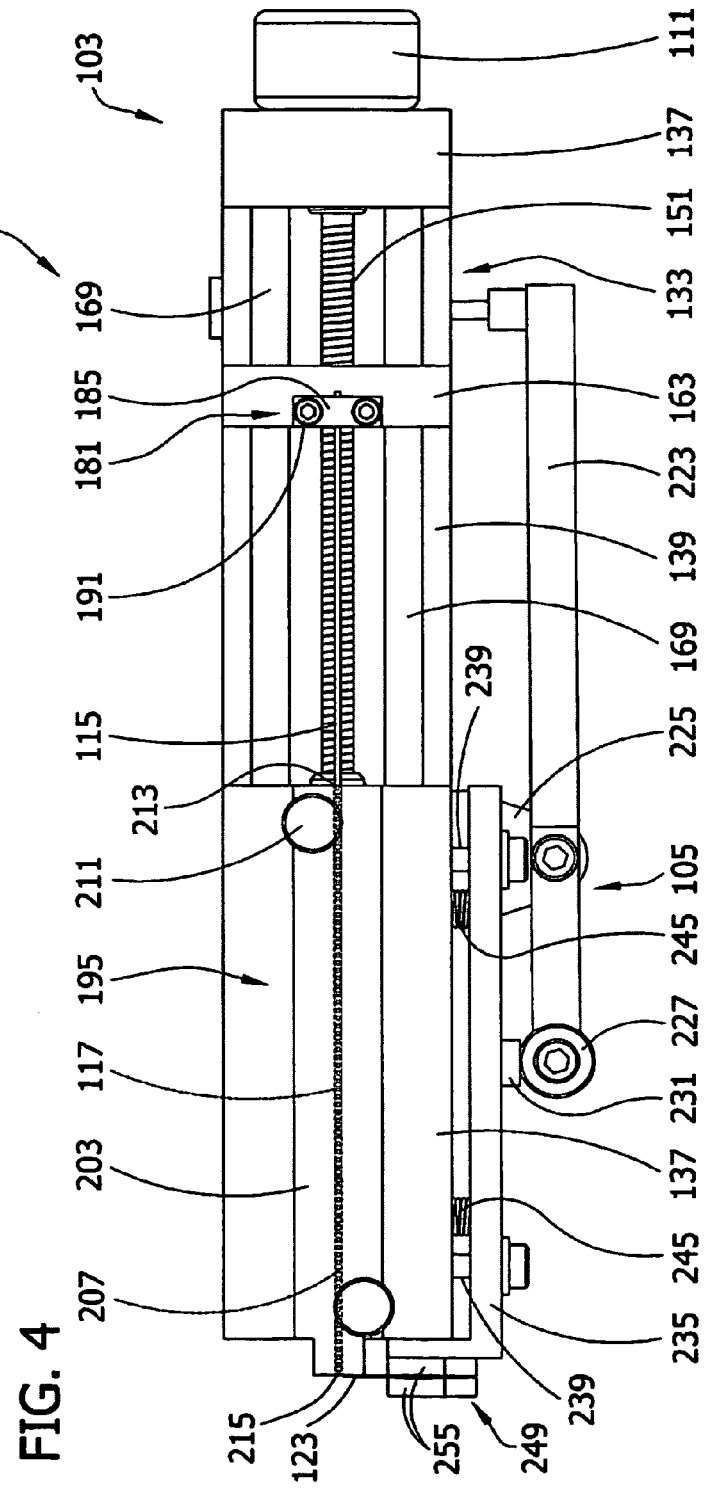
FIG. 4 is a top plan view thereof.
Figure 5:
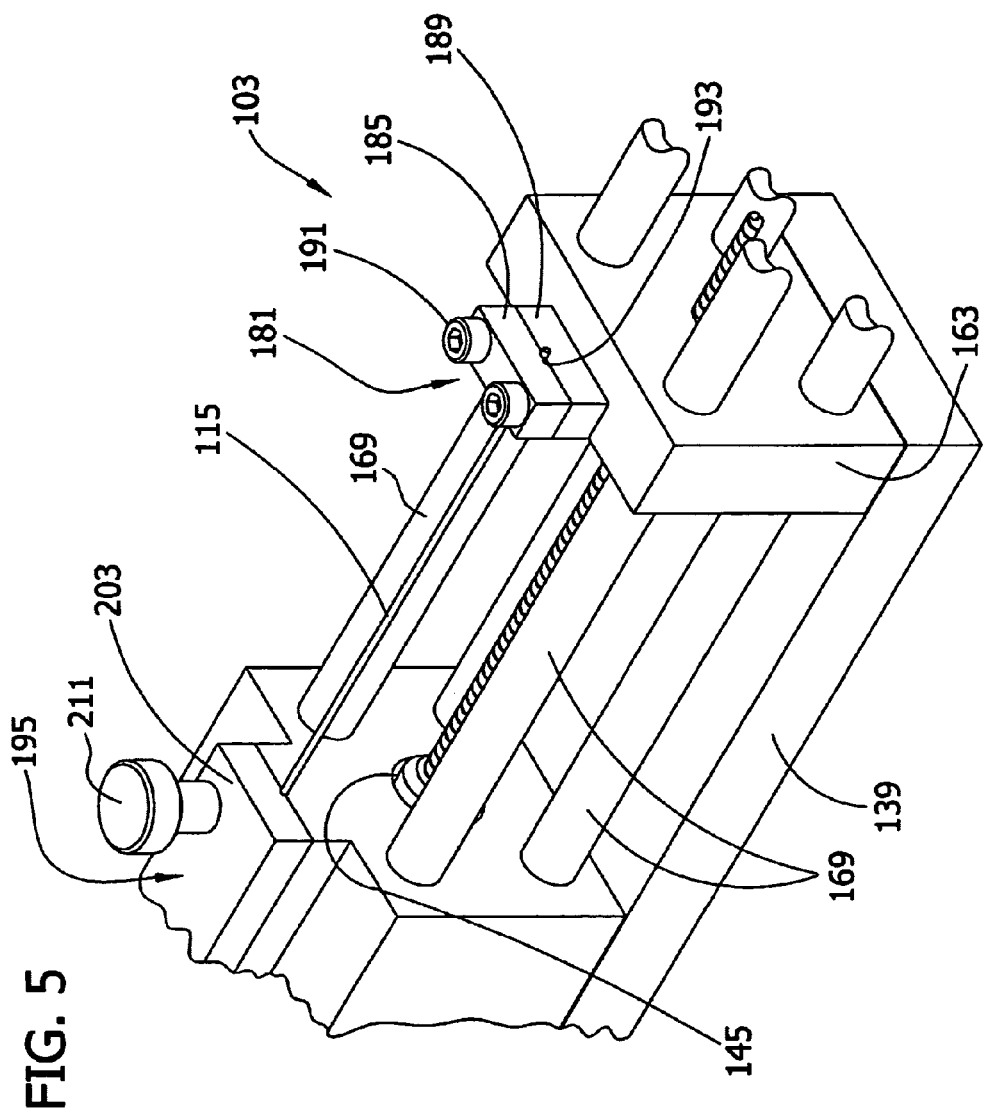
FIG. 5 is an enlarged fragmentary perspective of the apparatus.

A container holder 195 is also secured to the frame 133. The configuration of the container holder can be varied to suit various designs of the containers (e.g., micropipettes) from which the cellular pellet is to be extruded. In the embodiment shown in the drawings, for example, the container holder 195 comprises a two part housing 203 secured to the frame (e.g., by screws or other conventional fasteners 211). Referring to FIG. 4, the housing 203 defines a cavity 207 sized and shaped (e.g., generally cylindrically) for holding the container 117. When a container 117 is loaded in the holder 195, one end of a piston 115 can be inserted into the container through a rear opening 213 of the container and the other end of the piston can be secured to the drive block 163. Preferably, the diameter of the piston 115 is selected so there is a snug fit between the outside diameter of the piston and an inside diameter of the container 117.

An orifice 119 (FIG. 6) is formed at the end of the container holder 195. The orifice 119 is preferably aligned with the groove 193 in the piston mount 181, axis 179 of the piston 115, and the opening 213 at the rear of the container 117. More preferably, a line extending from the orifice 119 to any of the groove 193 in the piston mount 181, axis 179 of the piston 115, and the opening 213 at the rear of the container 117 is parallel to the axis 157 of the threaded shaft 151. The orifice 119 is an opening 215 at the front end of the container 117 as shown in FIG. 4. However, the orifice could be formed in other ways (e.g., by the end of a through-hole from a location adjacent the opening 215 at front end of the container 117 to the exterior of the housing) without departing from the scope of the invention. The orifice 119 preferably has a circular cross section. The diameter of the orifice is preferably between about 100 and about 600 microns, more preferably between about 200 and 400 microns.

In addition to the cutting blade 123, the cutting system 105 comprises an actuator 219 that is connected to the cutting blade 123 so that the actuator is operable to cause the cutting blade to reciprocate across the orifice 119, preferably in close proximity to (e.g., sliding contact with) the opening 215 at the front of the container 117. Various actuators are suitable for this job, including for example pneumatic actuators, hydraulic actuators, and motor-driven cams. In the embodiment shown in the drawings, for example, the actuator is a solenoid actuator 219 under the control of the control system 129.

Many different arrangements of gears and/or linkages can be used to connect the actuator 219 to the cutting blade 123 without departing from the scope of the invention. In the illustrated embodiment, the solenoid actuator 219 is positioned adjacent (e.g., in contact with) one end of a pivot arm 223, which is pivotally mounted to a pivot base 225 secured to the frame 133 so that the actuator is operable to rotate the pivot arm. The other end of the pivot arm 223 comprises a cam 227. A cam follower 231 is formed on a plate 235 which is slideably mounted on the frame 133. In the illustrated embodiment, the plate 235 is slideably mounted on a plurality of guide posts 239 (FIG. 4) secured to one of the blocks 137 of the frame 133. The plate 235 is preferably biased (e.g., by one or more springs 245 axially compressed between the plate and the frame 133) to move toward the cam 227.

A cutting blade holder 249 is secured to the plate 235. The cutting blade holder 249 is operable to hold the cutting blade 123 (e.g., a razor blade) so its cutting edge is adjacent the orifice 119 through which the pellet is to be extruded. In the embodiment shown in the drawings, the blade holder 249 comprises a blade mounting assembly 251 including two generally parallel plates 255 fastened together (e.g., by screws 259 or other suitably fasteners). The cutting blade 123 can be placed between the two plates 255 before they are fastened together so that the blade is secured to the mounting assembly 253 when the plates are fastened together. When so mounted, the cutting blade 123 is preferably flush against a sliding surface 261 formed on the side of the housing centered around the orifice 119 with the orifice 119 and oriented so the cutting edge of the cutting blade is adjacent the orifice.

To use the apparatus 101 to make a plurality of cell aggregates that are suitable for bio-ink particles, the container 117 (e.g., micropipette) containing a pellet comprising a plurality of cells, prepared as describe above for example, is loaded in the container holder 195 (FIG. 4). A piston 115 is inserted into the rear opening 213 of the container 117 and also secured to the drive block 163 via the piston mount 181. The motor 111 is activated to rotate the shaft 151 and thereby move the drive block 163—away from the motor, which causes the piston to move through the container 117 toward the orifice 119. Accordingly, the extruding system 103 begins extruding the pellet through the orifice 119.

The motor 111 is paused after a period of time (e.g., as determined by a timing system of the control system 129) to make the portion of the pellet that has been extruded through the orifice 119 stationary. While the motor 111 is paused, the control system 129 causes the cutting system 105 to cut the pellet adjacent the orifice 119 to thereby create a cell aggregate having a cylindrical shape. Preferably the control system 129 directs the motor 111 to paused upon formation of an extrusion having a length that is about equal (e.g., within about 10-20 microns of equal) to the diameter of the orifice 119 through which the pellet is being extruded to produce a cylindrical cell aggregate that has a diameter that is about equal to its length.

Figure 6:
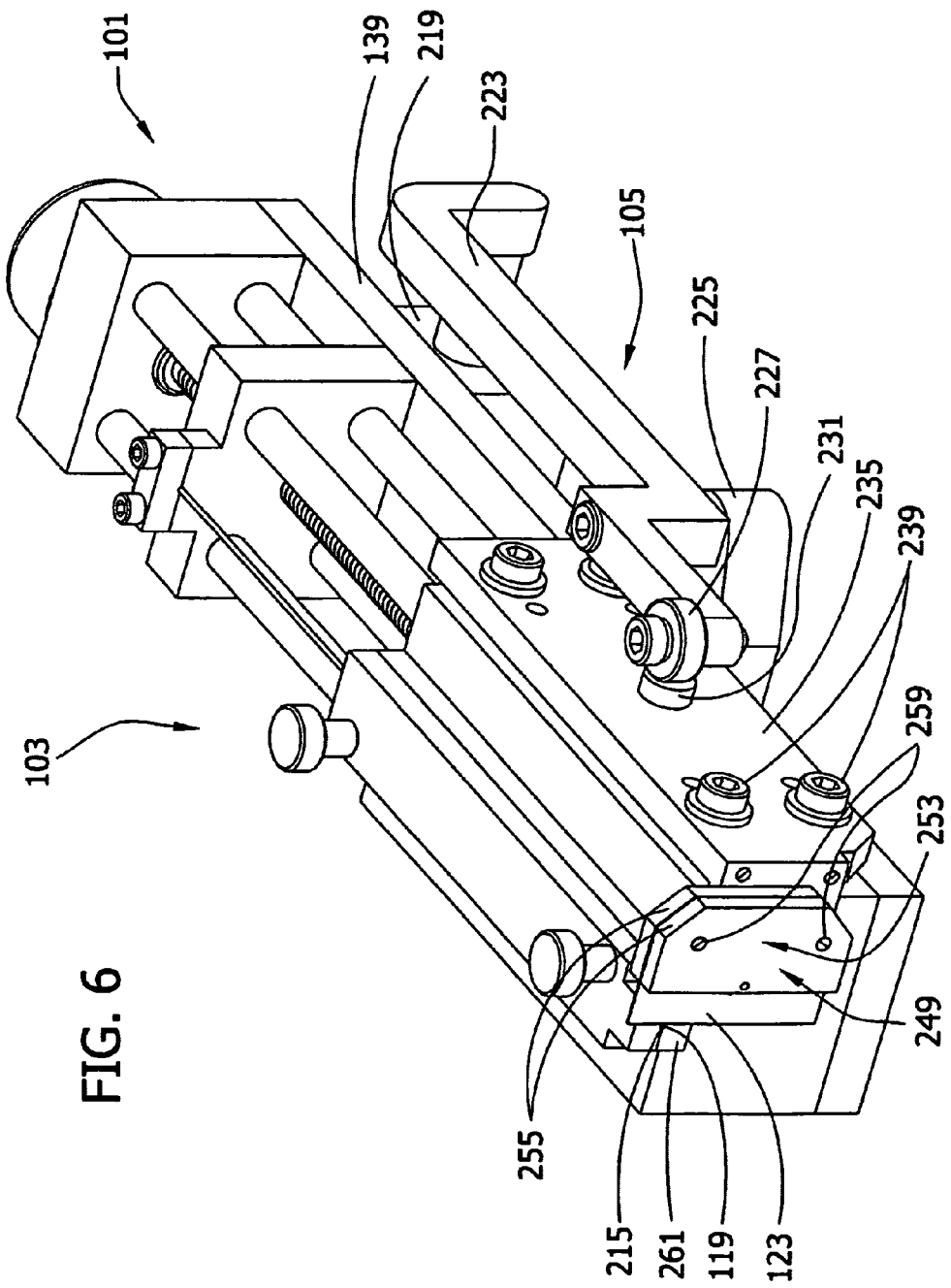
FIGS. 6 and 7 are perspectives of the apparatus showing a sequence of operation of a cutting system.
Figure 7:
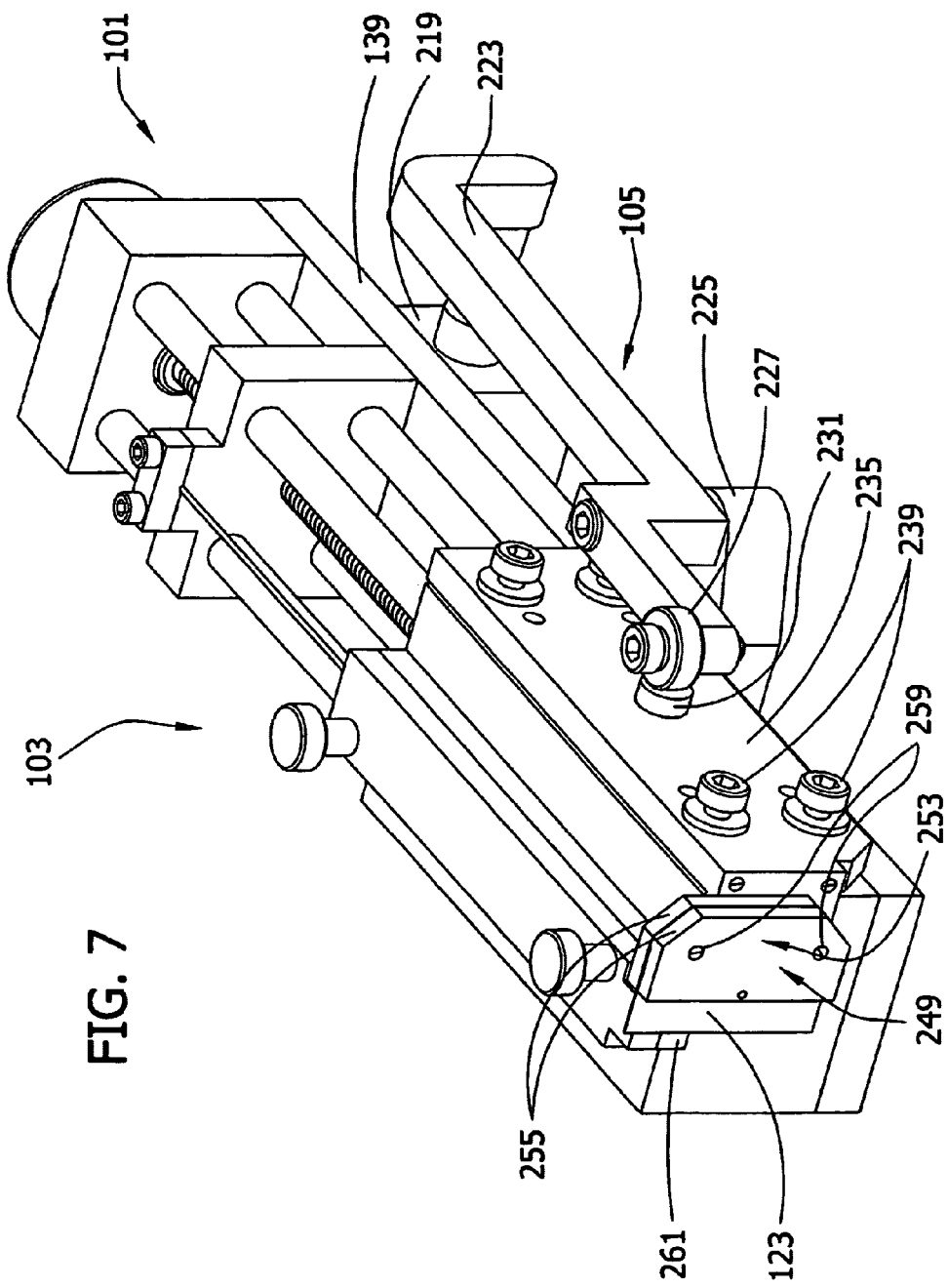

In the illustrated embodiment, for example, the cutting system is in an initial position as is depicted in FIG. 6. The control system 129 causes the cutting system 105 to cut the pellet by energizing the actuator 219. The actuator 219 rotates the pivot arm 223 to cause the cam 227 to push against the cam follower 231 to move the plate 235 against its bias. This causes the cutting edge of the cutting blade 123 to slide over the sliding surface 261 across the orifice 119, preferably within no more than about 2 microns of the opening 215 at the front end of the container 117, and more preferably flush against the front end of the container. As the cutting edge of the blade 123 moves across the orifice 119, it cuts (i.e., severs) the extruded part of the pellet (i.e., the extrudate) from the part of the pellet that is still in the container 119, thereby producing a cylindrical cell aggregate, which falls into a collection container (not shown) under the cutting blade 123. At this point the cutting system 105 is in the state depicted in FIG. 7. The collection container can contain a growth/support medium that is suitable for the particular cells in the cell aggregates. The collection container can also be agitated (e.g., on a gyratory shaker) if desired to produce spherical aggregates as described above.

After the cell aggregate has been cut, the control system 129 de-energizes the solenoid actuator 219, thereby allowing the bias of the plate 235 to move the plate away from the block 137, which causes the cutting blade 123 to return to the position it was in before the control system energized the solenoid. The movement of the plate 235 also rotates the pivot arm 223 in the opposite direction until the pivot arm is positioned as it was before the solenoid actuator moved it (FIG. 6). The motor 111 is restarted to resume extrusion of the pellet through the orifice 119. The process is repeated as long as desired or until the container 117 is empty. Each cycle preferably lasts for a period ranging from about 2 to about 3 seconds, resulting in production of cell aggregates at a rate ranging from between about 20 to about 30 aggregates per minute.

Control Unit

One embodiment of the control unit comprises a computer that contains information about the shape of a target organ and properties of one or more matrices and also provides instructions for the dispensing unit. For example, the computer control unit can store the anatomical "blueprints" (i.e., map) of target organs and the information on the desired biodegradable gels or polymers in relation to the bio-ink particles used. The blueprint can be derived from digitized image reconstruction of a natural organ or tissue. Imaging data can be derived from various modalities including noninvasive scanning of the human body or a detailed 3D reconstruction of serial sections of specific organs. The control unit may be the same control unit used to control the extrusion system and cutting system of the apparatus, as described above, but separate control systems could be used for the process of making the cell aggregates and the organ printing process without departing from the scope of the invention.

Dispensing Unit

In one exemplary embodiment, the dispensing unit is in electronic communication with and under the control of the control unit. The dispensing unit comprises a plurality of dispensers separately holding one or more compositions comprising bio-ink particles and one or more selected biodegradable gels or polymers. The dispensing unit also comprises a dispensing platform (e.g., a temperature-controlled substrate onto which the bio-ink particles and gels or polymers are deposited). The dispensing unit functions as a special purpose delivery device, capable of depositing bio-ink particles and biodegradable gels or polymers onto the dispensing platform, according to the instructions from the control unit.

Preferably, cell aggregates are loaded into one of the dispensers. For example, the cell aggregates can be aspirated into a dispenser (e.g., micropipette) one at a time. The dispenser is preferably a cylindrical container having an inner diameter that is about the same size as the diameter of the cell aggregates. As each cell aggregate is aspirated into the dispenser, a quantity of the suspension medium may also be aspirated into the dispenser. It is preferable to expel as much of the suspension medium as possible before aspirating the next cell aggregate. The result of this process is a single-file stack of cell aggregates lined up in the container and a minimal amount of the support medium. This arrangement facilitates controlled deposition of single cell aggregates by the dispenser. There is a limited time to dispense the cell aggregates before they fuse to each other.

A variety of printing or dispensing devices can serve as the dispensing unit, such as jet-based cell printers, cell dispensers or bio-plotters. For example, the dispensing unit disclosed in U.S. patent application Ser. No. 10/891,512 (Pub. No. 2004/0253365), the contents of which are hereby incorporated by reference, can readily be adapted for use in the present invention by re-dimensioning some of the dispensers (e.g., cartridges) so they are suitably sized to contain and dispense a composition comprising cell aggregates rather than individual cells. An instrument as described in the '512 application may be acquired from Sciperio, Inc. of Stillwater, Okla.

Maturation Unit

The maturation unit is a bioreactor that assures the proper post-process handling of the resulting construct. The maturation unit, depending on the complexity of the organ module, can comprise a simple incubator or a specifically designed bioreactor adapted to the particular needs of a specific organ printing process. This will depend in part on the type of tissue being produced as is well known to those skilled in the art.

Computer Modeling

The methods of the present invention can be used to reliability "print" a tissue having a desired structure. The invention can also facilitate selection of materials (e.g., cells and matrices) and other process variables (e.g., embedding patterns) that are best suited for the process.

When bio-ink particles are embedded in a matrix, the structural evolution of the cells depends on a number of variables including adhesive forces between the cells, adhesive and cohesive forces between the cells and the matrix, the characteristics of the matrix (including composition and spatial structure), and the pattern by which the cell aggregates are embedded in the matrix. Information about these variables can be used to run computer simulations to make useful predictions of the structural evolution. These predictions allow selection of combinations of biodegradable polymers or gels for use in forming the matrix, the particular bio-ink particles, and/or the embedding pattern by which the bio-ink particles are to be embedded in the matrix to be optimized for any specific organ printing process.

One embodiment of such a model considers the structural evolution of the cells comprising a plurality of cell aggregates that consists essentially of a single type of cell, after they are embedded in a uniform matrix. The model represents the cells and matrix elements as particles occupying the nodes of a discrete lattice (e.g., a cubic lattice). It uses information about specific interactions (e.g., the strength of adhesion or cohesion forces) between cells, cells and the matrix and between matrix volume elements. A three-dimensional model is constructed (e.g., a numerical model suitable for use in a computer simulation), in which the sites of a lattice are occupied either by point-like cells or matrix volume elements. For a model based on a cubic lattice, the total interaction energy, E of the system is written as $$E = \sum_{<r,r'>} J(\sigma_r, \sigma_{r'})$$

where r and r' label lattice sites, and <r,r'> signifies summation over neighboring sites, each pair counted once. First, second and third nearest neighbors are included, and it is assumed that a cell interacts with the same strength with all the 26 cells it comes into contact with. (26 is the total number of first, second and third nearest neighbors of a given site in a cubic lattice.) To specify occupancy, a spin value, $\sigma$, is assigned to each lattice site with values 0 for a "matrix particle" and 1 for a cell. The interaction energy of two neighbors, $J(\sigma_r, \sigma_{r'})$, may take either of the values $J(0,0)=-\epsilon_{gg}$, $J(1,1)=-\epsilon_{cc}$ or $J(0,1)=J(1,0)=-\epsilon_{cg}$. The positive parameters $\epsilon_{cc}$, $\epsilon_{gg}$ and $\epsilon_{cg}$ account for contact interaction strengths for cell-cell, matrix-matrix and cell-matrix pairs, respectively. More specifically, these are mechanical works needed to disrupt the corresponding bonds. (Note that $\epsilon_{cc}$ and $\epsilon_{gg}$ are works of cohesion, whereas $\epsilon_{gg}$ is work of adhesion per bond).

The strength of cell-cell interaction may be determined experimentally either directly or by measuring the tissue surface tension. The cell-matrix interaction is tunable by biochemical methods or by the concentration of a polymer forming the matrix. The matrix-matrix "bond energy" is an effective measure of matrix filament density, interaction and stiffness. It is determined by the specific chemistry of the matrix. For example, the matrix-matrix interaction can be evaluated by measuring the viscoelastic moduli (e.g., the loss and/or storage modulus) of the matrix. The cell-matrix interaction can be evaluated in the same way, by measuring how the viscoelastic moduli of the matrix is affected by introduction of cells into the matrix.

The foregoing energy equation may be rewritten by separating interfacial and bulk terms in the sum:

$$E = \gamma_{cg} B_{cg} + \text{const.}$$

where $B_{cg}$ is the total number of cell-matrix bonds, and $\gamma_{cg}=(\epsilon_{cc}+\epsilon_{gg})/2-\epsilon_{cg}$ is proportional to the cell-matrix interfacial tension. The remaining terms in E do not change as the cellular pattern evolves.

The structural evolution of the system can be predicted using Monte Carlo simulations, relying on a random number generator. One cell on the aggregate-matrix interface is selected at random and exchanged with a randomly selected adjacent matrix volume element. The corresponding change in total interaction energy, $\Delta E$, is calculated and the new configuration accepted with a probability P=1 if $\Delta E \leq 0$ or $P=\exp(-\beta \Delta E)$ if $\Delta E>0$. $\beta=1/E_T$, is the inverse of the average biological fluctuation energy $E_T$, analogous to the thermal fluctuation energy, $k_B T$ ($k_B$—Boltzmann's constant, T—absolute temperature). In statistical mechanics the thermal fluctuation energy characterizes thermal agitation in a system of atoms or molecules. In the case of cells, it is a measure of the spontaneous, cytoskeleton driven motion of cells, able to break adhesive bonds between neighbors via membrane ruffling, or more generally, via membrane protrusive activity (e.g., filopodial extensions). By definition, a Monte Carlo step (MCS) is completed when each cell at the cellular material-matrix interface has been given the opportunity to move once. During each MCS the interfacial sites are selected in random order. The matrix boundary is treated as a fixed physical limit of the system, and cells are constrained to move within the matrix.

Depending on the properties of the polymers or gels used to form the matrix, the characteristics of the bio-ink particles, and the embedding pattern, the bio-ink particles represented in the model may or may not evolve into a desired structure. In some cases the constituent cells disperse into the surrounding matrix. In other cases, the constituent cells may quickly collapse into an undesired structure.

Some structures of cells embedded in a matrix correspond to long-lived structures, the energies of which are approximately constant for a large number of MCS (See FIG. 11 discussed later herein in connection with the examples). They correspond to the structure of the model associated with plateaus in the plot of the total interaction energy vs. the number of MCS. The Monte-Carlo method does not account for passage of time per se, but the number of MCS is generally correlated with passage of time so that structures that are relatively stable for many MCS can be determined to be long-lived. Long-lived structures are important for tissue engineering, because they suggest that the physical system represented by the model can evolve into the long-lived structure indicated by the model. Then the fused aggregates can be separated from the matrix (e.g., by degrading the matrix by exposure to heat, light or any other stimulus effective to degrade the particular matrix) to obtain a tissue having the same general structure as the long-lived structure by the model.

The model can be generalized as necessary to simulate other physical systems involving the structural evolution of the cells of a plurality of cell aggregates embedded in a matrix. Thus, the computer simulation can readily be adapted for use in predicting structural evolution for more complicated organ printing processes using the principles set forth above. For example, the matrix can comprise a plurality of different substances having distinct properties and/or the cell aggregates may comprise different cell types having different characteristic interactions with the matrix (or the various components thereof). To account for these additional variables, the total interaction energy equation is simply revised to account for the various different kinds of interaction forces at work in the system.

Consider, for example, that the physical system represented by the model is a cylindrical congregation of cell aggregates comprising cells of two types (e.g., multi-color bio-ink; wherein the first type are epithelial cells are the second type are smooth muscle cells) embedded in a matrix comprising a volume of a first substance, which is supportive of the cells of the first type, forming a core through the cell aggregates and a volume of a second substance, which is supportive of the cells of the second type, surrounding the cells aggregates and the volume of the first substance. Notably, this physical system could represent an organ printing process for production of a tubular organ wherein the first type of cells form the lumen and the second type of cells form smooth muscle surrounding the lumen. The energy equation can be modified to account for the various interactions in the total energy equation including: (1) cells of the first type with cells of the first type; (2) cells of the first type with cells of the second type; (3) cells of the first type with the first substance; (4) cells of the first type with the second substance; (5) cells of the second type with the cells of the second type; (6) cells of the second type with the first substance; (7) cells of the second type with the second substance; (8) volume elements of the first substance with other volume elements of the first substance; (9) volume elements of the second substance with other volume elements of the second substance and (10) volume elements of the first substance with other volume elements of the second substance.

By executing computer simulations to predict how the structural evolution of constituent cells of a plurality of cell aggregates embedded in a matrix according to an embedding pattern changes as process variables (including, for example, the type of cells used to form the cell aggregates, the substances used to form the matrix, and the size, shape and configuration of the embedding pattern) change, one can determine whether a particular combination of cell aggregates, matrix, and embedding pattern is likely to allow a desired tissue structure to be produced without running an actual experiment on a real physical system. Further, an understanding of how the cellular pattern evolves in a series of modeled experiments based on differing process variables can be used to optimize process variables to obtain a better result.

For example, the modeling methods may indicate that results would improve if the adhesion of the cells could be modified by some factor. Similarly, the model methods may indicate that the size of geometric elements of the embedding pattern need to be adjusted (e.g., to account for contraction of the structure). Likewise, the modeling methods may indicate that using a matrix having different properties would lead to more desirable results.

Thus, in one embodiment of the invention, the methods described above are used to predict how various matrix candidates will perform when a plurality of cell aggregates are embedded in the candidate matrices according to a specified embedding pattern. One of the candidate matrices exhibiting the best results in the modeling can be selected for use in producing a plurality of fused cell aggregates having a desired three-dimensional structure. In another embodiment of the invention the modeling methods are used to predict how various candidate cell types will perform when a plurality of cell aggregates comprising candidate cells are embedded in a specified matrix according to a specified embedding pattern. One of the cell candidates exhibiting the best results in the modeling can be selected for use in producing a plurality of fused cell aggregates having a desired three-dimensional structure. In still another embodiment of the invention the modeling methods described above are used to predict the performance of various candidate embedding patterns when a plurality of cell aggregates are embedded in a specified matrix in accordance with the candidate embedding patterns. One of the candidate embedding patterns exhibiting the best results in the modeling can be selected for use in producing a plurality of fused cell aggregates having a desired three-dimensional structure. Moreover, the modeling methods can be adapted to predict performance of various candidate combinations of cells, matrices, and embedding patterns. One of the combinations of cells, matrices, and embedding patterns exhibiting the best results in the modeling can be selected for use in producing a plurality of fused cell aggregates having a desired three-dimensional structure.

Method of Organ Printing

According to one embodiment of the present invention a layer of a matrix (e.g., a solidifying bio-degradable gel or polymer having known properties) is deposited on a substrate. The layer of matrix may comprise a uniform layer of a single substance or it may comprise multiple substances deposited to form the layer according to a pre-determined pattern. A plurality of cell aggregates are embedded in the layer according to a pre-determined pattern. Optionally, the matrix and the cell aggregates are deposited simultaneously. The thickness of the layer is preferably about the same as the diameter of the cell aggregates. The cell aggregates can comprise cell aggregates that contain multiple cell types (e.g., a mixture of at least two types of cells). The cell aggregates can also comprise one cell aggregate cells consisting essentially of a single type of cells (e.g., epithelial cells) and another cell aggregate consisting essentially of a single type of cells (e.g., connective tissue forming cells) having different properties. It is understood that some cell aggregates, such as those consisting essentially of connective tissue forming cells, can include a matrix substance (i.e., an extra-cellular matrix) and still be considered to consist essentially of a single type of cells.

These two steps are then repeated as necessary to embed cell aggregates in the matrix, layer-by-layer, according to an embedding pattern that is predicted to result in a cellular pattern evolving into a plurality of fused cell aggregates forming a desired three-dimensional structure. The embedded cell aggregates are placed in the maturation unit, in which pattern evolution takes place resulting in the cell aggregates fusing and forming the desired tissue or organ geometry. If the cell aggregates comprise multiple cell types, this can result in the cells segregating into different distinct populations of cells. When the cells have evolved into a tissue structure having the desired structure, the tissue structure can be separated from the matrix via standard procedures for melting or dissolving the matrix.

Using bio-ink particles as building blocks instead of isolated cells has several advantages. First, using bio-ink particles can significantly reduce the processing (actual printing) time to achieve the desired structure. Reduced processing time enhances cell survival. Second, using a plurality of cells (e.g., multitude of cells) in a more physiological environment (i.e., allowing the cells to adhere to each other or the aggregate matrix) provides better conditions to achieve a high concentration of healthy cells, which is difficult to achieve by other methods. Third, because bio-ink particles may contain several cell types and a pre-built internal structure, it is easier to engineer desired structures and considerable time can be saved during post-process tissue and organ maturation. Finally, the mechanical hardship involved in the dispensing process is less damaging for bio-ink particles than for individual cells.

EXAMPLES

Example 1

Cell Aggregate Preparation

Chinese Hamster Ovary (CHO) cells, transfected with N-cadherin (courtesy of A. Bershadsky, Weizmann Institute, Rehovot, Israel), were infected with histone binding $H_2B$-YFP retrovirus (provided by R. D. Lansford, Beckman Institute at California Institute of Technology). Confluent cell cultures (3-4×10⁶ cells/75 cm² TC dish) grown in Dulbecco's Modified Eagle Medium (DMEM, Gibco BRL Grand Island, N.Y.; supplemented with 10% FBS (US Biotechnologies, Parkerford, Pa.), 10 μg/ml of penicillin, streptomycin, gentamicin, kanamycin, 400 μg/ml geneticin), were washed twice with Hanks' Balanced Salt Solution (HBSS) containing 2 mM $CaCl_2$, then treated for 10 minutes with trypsin 0.1% (diluted from 2.5% stock, Gibco BRL, Grand Island, N.Y.). Depleted cells were centrifuged at 2500 RPM for 4 minutes. The resulting pellet was transferred into capillary micropipettes of 500 μm diameter and incubated at 37 C.° with 5% $CO_2$ for 10 minutes. The firm cylinders of cells removed from the pipettes were cut into fragments (500 μm height) using an automated cutting device, then incubated in 10-ml tissue culture flasks (Bellco Glass, Vineland, N.J.) with 3 ml DMEM on a gyratory shaker at 120 RPM with 5% $CO_2$ at 37° C. for 4 hours. This procedure provided substantially spherical aggregates of substantially uniform size (~500 μm diameter). This procedure has been used to produce substantially spherical aggregates of substantially uniform size having different diameters as well.

Example 2

Formation of a Fused Ring Structure

The cell aggregates prepared in Example 1 were used to engineer a three dimensional tissue construct by either "manually printing" or using computer controlled delivery devices to print (i.e., embedding) the aggregates into biocompatible gels in a predetermined pattern.

NeuroGel™ (a biocompatible porous poly[N-(hydroxypropyl)methacrylamide] hydrogel) disks of 10 mm diameter and 2 mm thickness, containing RGD fragments (provided by Stephane Woerly, Organogel Canada, Quebec) were washed three times with DMEM to eliminate the storage medium. A 0.5 mm wide, 0.5 mm deep circular groove was cut into a disk. Ten aggregates were placed (either manually or by printing using a device as described herein) contiguously in the groove to form a closed circle. The groove was refilled with the gel to completely embed the aggregates. This structure was incubated at 37° C., 5% $CO_2$ for 72 hours in a tissue culture dish containing 10 ml DMEM, washed with PBS, and finally embedded in Tissue-Tek® OCT Compound (Electron Microscopy Sciences, Fort Washington, Pa.). The structure was slowly cooled (1 C.°/min) to −20 C.° in a Nalgene freezing container (Nalgene Labware, Rochester, N.Y.). To visualize aggregate fusion, at the end of the experiment, cryosectioning was performed with a Reichert 2800N Frigocut cryotome (Reichert Jung, Arnsberg, Germany), yielding 10-16 micron thin slices mounted on microscope slides. Slices were examined on an Olympus IX-70 inverted microscope with fluorescent attachment at 4× magnification. The results are shown in FIGS. 8C and 8D.

To tune the strength of cell-gel interaction, further fusion experiments were conducted using rat-tail collagen type I (Sigma-Aldrich, St. Louis, Mo.). The collagen was dissolved in 1N acetic acid, and then treated with Ham's F12 medium with sodium bicarbonate. At room temperature this mixture gels in a few minutes depending on concentration. The gel-aggregate structure was achieved by creating a ring of ten aggregates placed contiguously on the top of a previously (almost) solidified collagen layer, then covering the aggregates with liquid collagen that embedded the aggregates after gelation. These samples were incubated under the same conditions as described above. This process was performed using 1.0, 1.2 and 1.7 mg/ml collagen. The resulting samples were transparent, thus it was possible to follow pattern (i.e., toroid) evolution in time by phase contrast and fluorescent microscopy. Cell survivability was checked with Trypan Blue (Invitrogen, Carlsbad, Calif.) at the end of each fusion experiment. A minimal number of uniformly distributed dead cells were found. The results are shown in FIGS. 8E-8J.

Results

The experiments were carried out by the system described herein. The experiments were performed with fixed cell-cell adhesion and varying gel properties, by depositing or printing N-cadherin transfected CHO cell aggregates into NeuroGel™ disks and 1.0, 1.2, and 1.7 mg/ml. collagen. As indicated by the teachings of the invention, the ability of aggregates to fuse depends on the mutual properties of the cell aggregates and gel or polymers, as expressed by the parameter $\gamma_{cg}/E_T$ in the model. The transfected CHO cells' adhesive properties were quantitatively assessed, by measuring aggregate surface tension using techniques such as those described in Foty, et al., *Dev. Biol.* 278:255-63 (2005). The relative importance of cell-cell and cell-matrix interactions has also been investigated quantitatively. See, e.g., P. L. Ryan, et al., PNAS 98, 4323-4327 (2001).

FIGS. 8A-8L show initial (FIGS. 8A, 8C, 8E, 8G, 8I, and 8K) and final (FIGS. 8B, 8D, 8F, 8H, 8J, and 8L) cell aggregate configurations in both simulations and in the experiments using the various biocompatible gels. FIGS. 8A-8B and 8K-8L correspond to simulations that were run using the model described herein, with $\gamma_{cg}/E_T=0.9$ and $\gamma_{cg}/E_T=0.25$, respectively. The ten aggregates, each containing 925 cells were one cell diameter from each other in the starting configurations. The final configurations were reached after 25,000 and 50,000 MCS, respectively.

The results of the simulation show that evolution of the cellular pattern is governed by a single parameter, $\gamma_{cg}/E_T$, which for cells with specific adhesion apparatus, is controlled by the chemistry of the gel. The theoretical analysis shows that, once gel properties are appropriately tuned, efficient fusion of adjacent aggregates takes place. For small $\gamma_{cg}/E_T$ (=0.25 in panels K-L) cells can spread in the bulk of the gel and the pattern evolves towards its lowest energy state, being a sphere. Under optimal cell-gel interface properties, for example, as depicted in FIGS. 8A-8B ($\gamma_{cg}/E_T=0.9$), fusion of aggregates results in a 3-dimensional toroidal structure.

FIGS. 8C-8D, 8E-8F, 8G-8H and 8I-8J correspond to the experimental results using the CHO cell aggregates embedded in a NeuroGel™ disk and in collagen gels of concentration 1.0, 1.2, and 1.7 mg/ml respectively. FIGS. 8I-8J show that collagen at concentration of 1.7 mg/ml is analogous to a permissive scaffold with small $\gamma_{cg}/E_T$. Collagen at concentration of 1.0 and 1.2 mg/ml match more the definition of the non-permissive gel with high $\gamma_{cg}/E_T$. These gels favor much less (collagen), or not at all (neurogel), the dispersion of the cells into the scaffold, thus facilitating fusion.

Figure 9A:
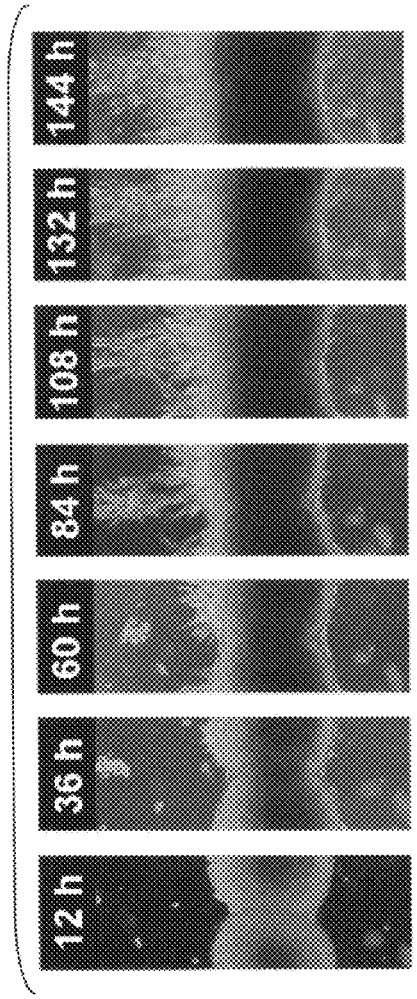
FIG. 9A shows the boundary between two adjacent aggregates in a ring structure (FIGS. 9B and 9C) embedded in 1.0 mg/ml collagen gel at various times, as described in Example 2.
Figure 9C:
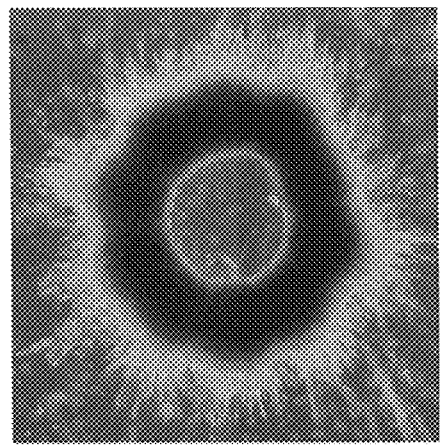
Figure 9B:
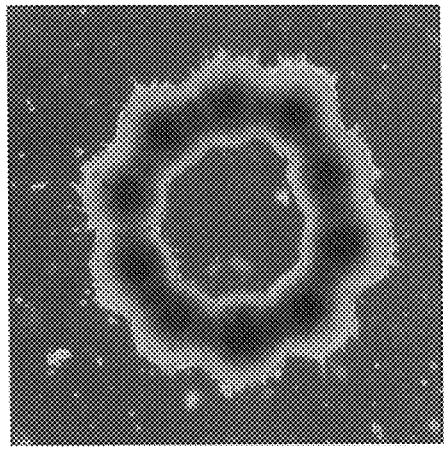
Figure 10:
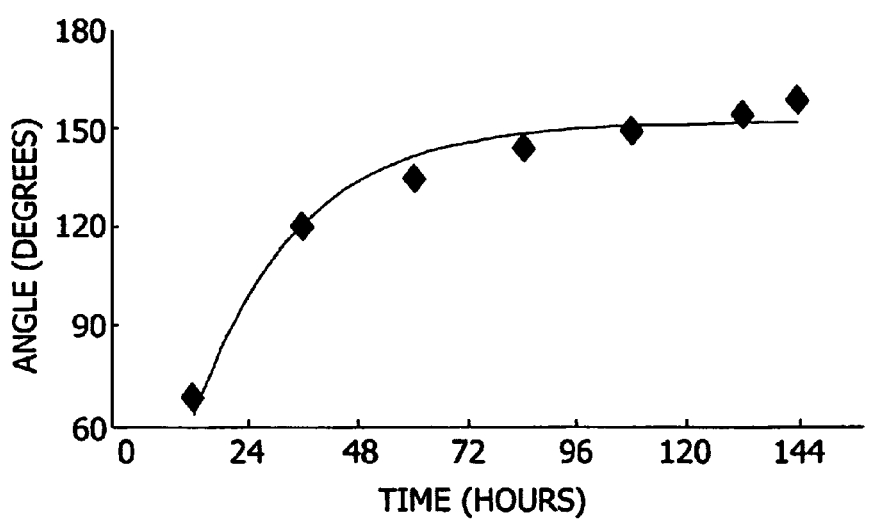
FIG. 10 is a plot of the angle between the tangents to the boundaries of the adjacent aggregates vs. time, as described in Example 2.

FIG. 9A shows the time variation of the boundary between two adjacent aggregates in the 1.0 mg/ml collagen gel (see FIGS. 9B and 9C). A measure of fusion is the instantaneous value of the angle formed by the two aggregates. As aggregates coalesce, the angle between the tangents to their boundaries (drawn from the point where they join) approaches 180°. The curve in FIG. 10 is an exponential fit to the data in the form $C[1-\exp(-t/\tau_{cc})]$ (C—constant), with $\tau_{cc} \approx 23$ h. Here the quantity $\tau_{cc}$ defines a time scale of aggregate fusion.

Example 3

Identification of a Long-Lived Structure

Figure 11A:
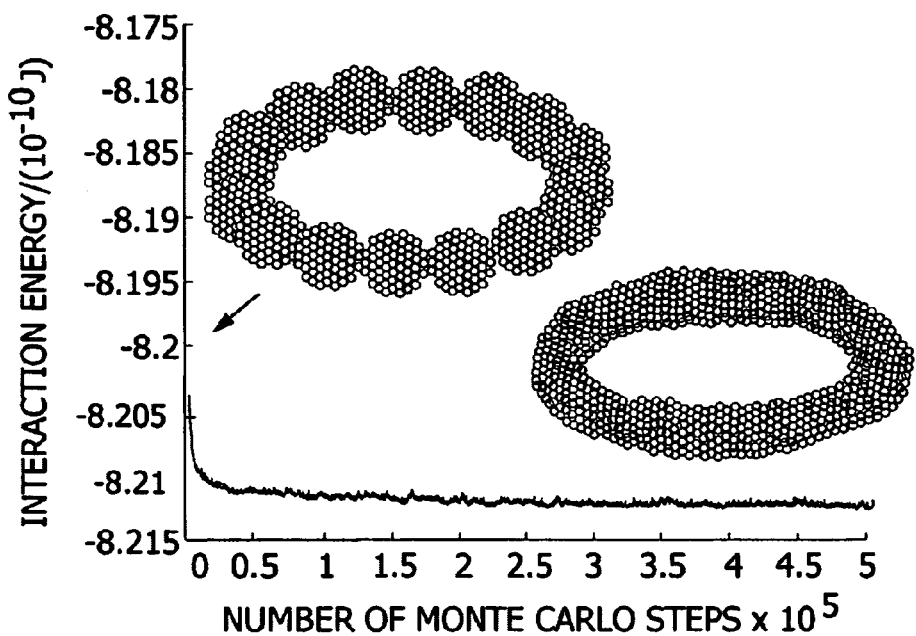
FIGS. 11A-11B are plots (at different scales) of total interaction energy vs. number of Monte Carlo steps, for the simulation in Example 3.
Figure 11B:
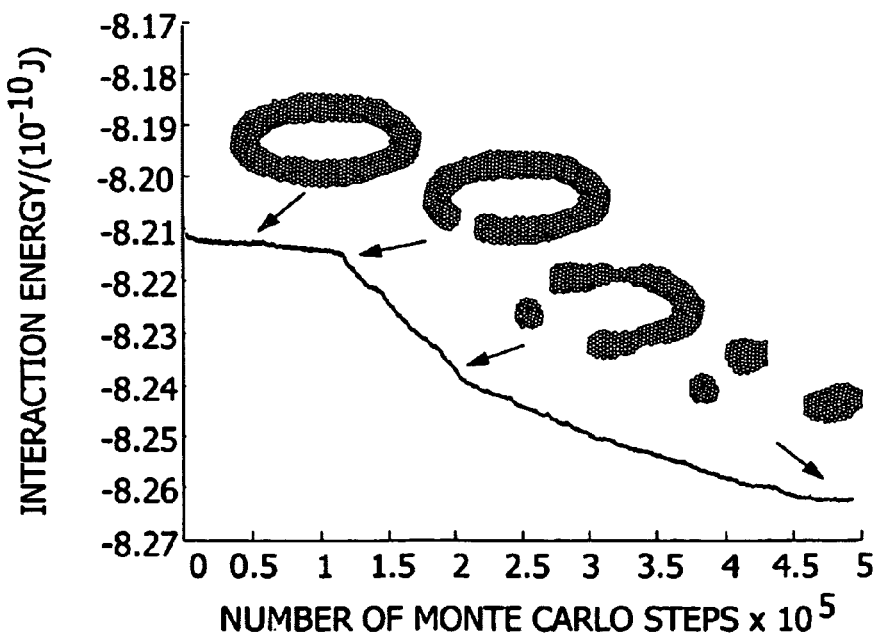

Shapes corresponding to long-lived structures (e.g., toroidal structures), may be identified from plateaus in the plot of the total interaction energy vs. MCS. This is illustrated in more detail in the simulation shown in FIG. 11A and FIG. 11B ($\gamma_{cg}/E_T$=1.1), where the initial state progresses towards a long-lived toroidal configuration, whose energy is essentially unchanged in the entire interval between $10^4$ and $6 \times 10^4$ Monte Carlo steps (MCS) (FIG. 11A). Eventually the toroid becomes unstable, and at about $10^5$ MCS it ruptures (FIG. 11B). Subsequent massive rearrangements lead to a pronounced energy decrease while the system evolves into three rounded aggregates. These remain stable for a long time because large spatial separations hinder their fusion into a single spheroid.

Once a structure reaches the long-lived state, it can be stabilized by dissolving the supporting gel or polymer. In the simulations this corresponds to increasing the value of $\gamma_{cg}/E_T$. Indeed, if in the simulation shown in FIG. 11A this quantity is changed to $\gamma_{cg}/E_T$=2 anywhere in the plateau region, the energy remains constant as long as the simulation is run.

Example 4

Model Fusion of a Ring Structure and Formation of a Cellular Tube

Fusion of a ring structure and formation of a cellular tube were simulated using the models described) herein, to demonstrate the ability of these models to predict aggregate fusion and structure formation based on varying parameters.

Modeling Biological Structure Formation Based on Tissue Liquidity

Figure 12:
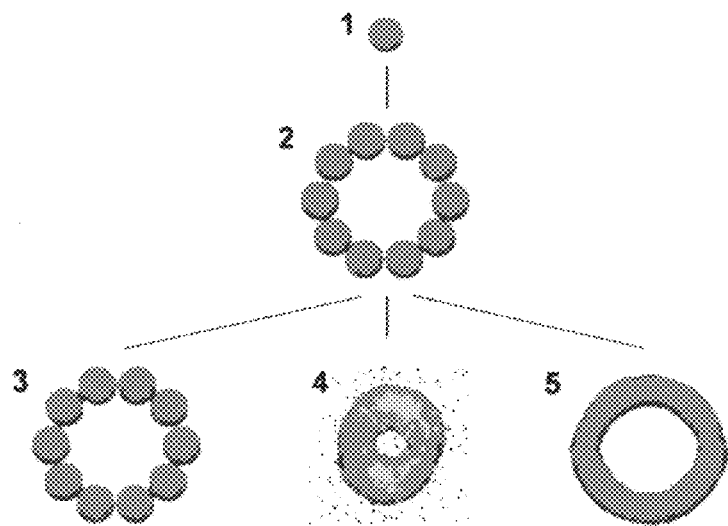
FIGS. 12 and 13 are sequences of modeling images showing the simulation of ring structure formation (FIG. 12) and tube formation (FIG. 13), as described in Example 4.

The fusion of contiguously arranged aggregates into a ring structure was simulated for varying interfacial tensions between the embedding gel and cellular material using the model described herein. Referring to FIG. 12, ten aggregates 1201 of 4169 cells each were contiguously arranged into an initial ring pattern 1202. Simulations were then run on the initial ring structure using varying values for $\gamma_{cg}/E_T$. The results 1203, 1204, 1205 were recorded photographically.

The results of the simulations indicate that the ability of the ring of aggregates to fuse depends on the interfacial tension, $\gamma$, between the embedding gel (not shown) and the cellular material. The structure 1203 was the resulted when $\gamma_{cg}/E_T$=10 (analogous to agarose gel). $E_T$ is the average biological fluctuation energy, which is analogous to the thermal energy in true liquids. $E_T$ is a measure of the spontaneous, cytoskeleton driven motion of cells (see Mombach, et al., *Phys. Rev. Lett.* 75, 2244-2247 (1995)), and its value depends on cell type. The structure 1204 was the result when $\gamma_{cg}/E_T$=0.25 (analogous to 1.7 mg/ml collagen gel). The structure 1205 was the result when $\gamma_{eg}/E_T$=0.9 (analogous to 1.0 mg/ml collagen gel).

Figure 14:
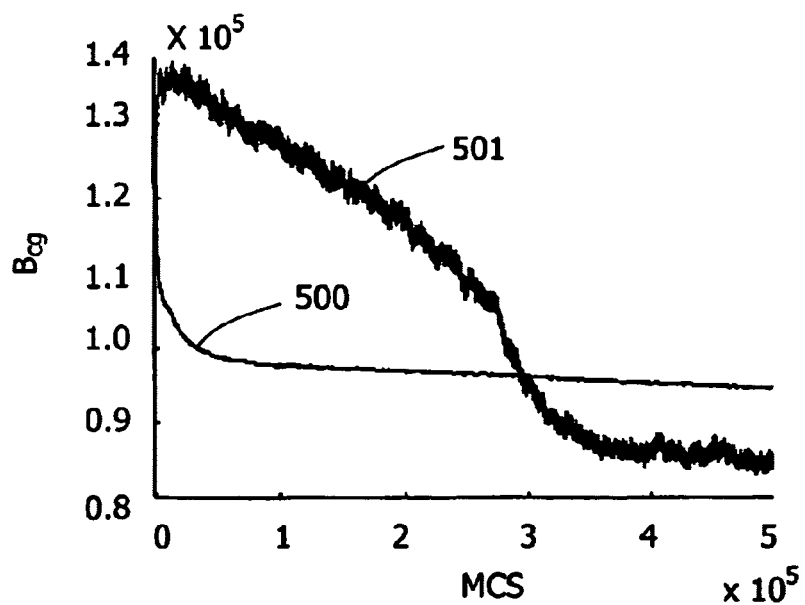
FIGS. 14 and 15 are plots of $B_{cg}$ vs. number of Monte Carlo steps for a simulation of ring structure formation (FIG. 14) and tube formation (FIG. 15), as described in Example 4.

The results indicate that if $\gamma$ is high (e.g., $\gamma_{cg}/E_T$=10), cells are unable to move and the initial configuration remains practically frozen (i.e., no fusion takes place) as indicated by the structure 1203. If the interfacial tension is small (e.g., $\gamma_{cg}/E_T$=0.25) cells can easily migrate into the gel and the system is able to reach its true lowest energy state, a single spherical configuration, as indicated by structure 1204. Finally, for intermediate values of γ (e.g., $\gamma_{cg}/E_T$=0.9) a long-lived fused ring forms, as indicated by structure 1205. During evolution of the long-lived structure 1205, the number of cell-matrix bonds, $B_{cg}$ remains practically unchanged for many thousands of Monte Carlo steps (MCS), as evidenced by the curve (500) in FIG. 14. In the present model $B_{cg}$ is a quantity related to the overall energy and proportional to the surface area of the structure. Changes in the slope of $B_{cg}$ vs. MCS correspond to modifications in construct topology. In the studied range of MCS these are more frequent for $\gamma_{cg}/E_T$=0.25, as evidenced by the curve (501) in FIG. 14, due to faster pattern evolution. The final configurations shown in FIGS. 12(3), (4) and (5) were reached in $2.5 \times 10^5$ MCS.

Model Cellular Tube Formation

Figure 13:
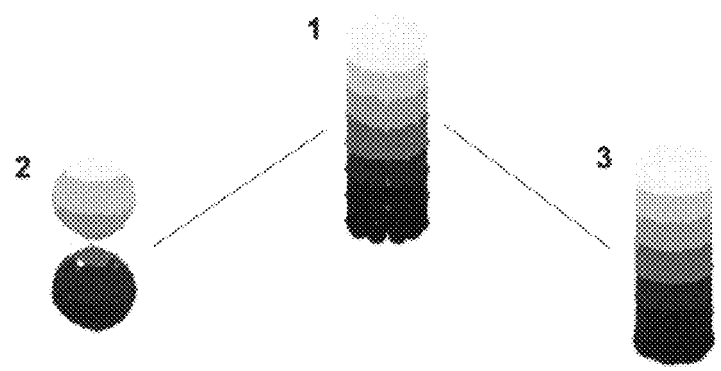

The formation of a cellular tube from an initial state comprising 15 layers of cellular rings was simulated using the model described herein (FIG. 13). Ten aggregates comprising 257 cells each were placed contiguously along circles to form a ring. A second ring layer, again comprising ten contiguous aggregates of 257 cells each, was closely packed in the vertical direction on the first ring layer, so that each aggregate in the second ring touched two other aggregates from below. This was repeated until a structure 1301 comprising 15 layers of rings was simulated. Simulations for the resulting 15 layer structure 1301 were then run, using varying-values for $\gamma_{cg}/E_T$. The resulting structures 1302, 1303 were recorded.

Figure 15:
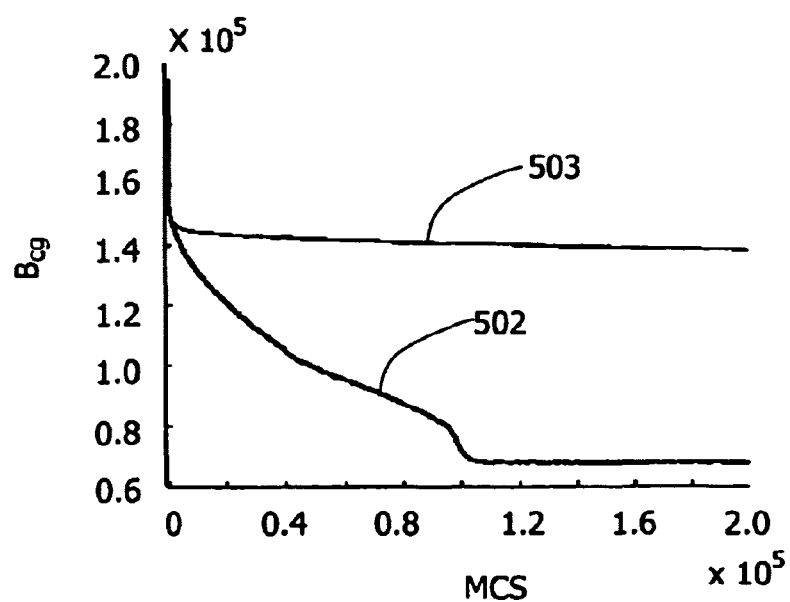
Figure 16:
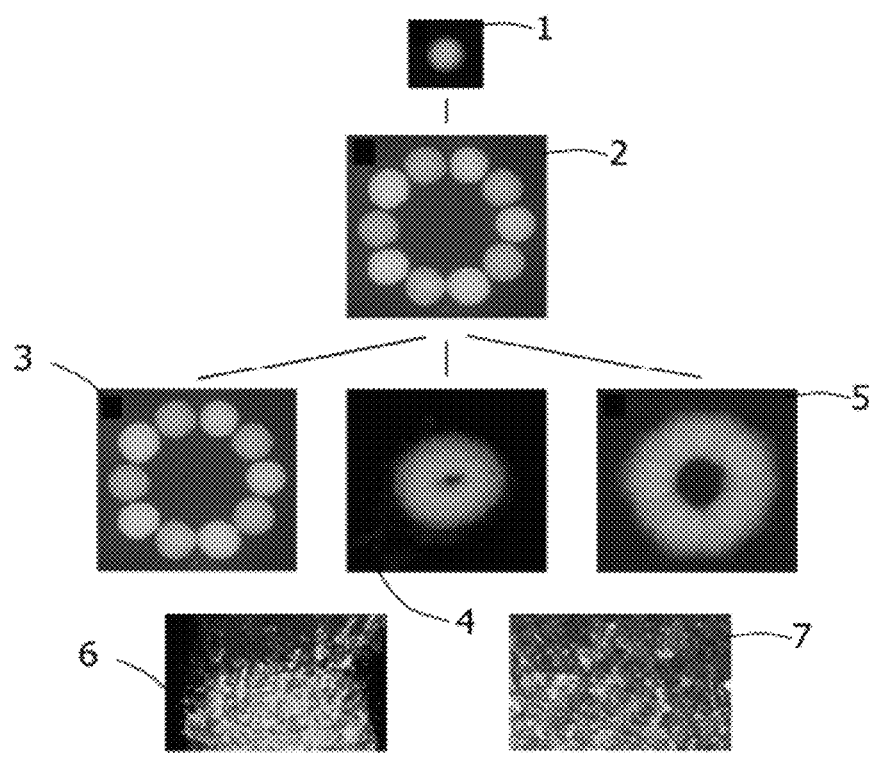
FIG. 16 is a fluorescent image showing ring structure formation when fluorescently labeled cell aggregates are embedded in agarose gel, 1.7 mg/ml collagen gel, and 1.0 mg/ml collagen gel, an image of the fusion of two neighboring aggregates embedded in 1.0 mg/ml collagen gel, and an enlarged view of the contact region between two fused aggregates embedded in 1.0 gm/ml collagen, as described in Example 5.

When $\gamma_g/E_T$=0.4, the 15 layer structure 1301 breaks up into two spheroids 1302 and remains in this state for a prolonged period of time, as evidenced by the curve (502) in FIG. 15. The relatively large spatial separation between the spheres makes their fusion into a single structure difficult. When $\gamma_{cg}/E_T$=2, after $2 \times 10^5$ MCS the 15 layer structure 1301 fuses to form a tube 1303, which is a robust, long-lived structure, as evidenced by the curve (503) in FIG. 15.

Example 5

Formation of a Fused Ring and Fused Tube Structure Using Fluorescently Labeled Cell Aggregates Formation of a Fused Ring Structure CHO cells as described in Example 1 were fluorescently labeled with two different membrane intercalating dyes of different color, in order to better illustrate cell aggregate fusion process.

Prior to aggregate formation, the CHO cells were stained with either PKH26 Red Fluorescent General Cell Linker or PKH2 Green Fluorescent General Cell Linker (Sigma, St. Louis Mo.) as recommended by the manufacturer. The procedure described in Example 1 was repeated using these fluorescently labeled CHO cells, to form fluorescently labeled CHO cell aggregates of approximately 480 microns in diameter. The cell aggregates 1601 comprised about 40,000 cells per aggregate.

Ten of the fluorescently labeled cell aggregates were contiguously arranged (either manually or printed using the device described herein) to form a closed circle 1602 on either agarose gel, 1.7 mg/ml collagen, or 1.0 mg/ml collagen, as prepared in Example 2. The aggregates were arranged in an alternating ring structure 1602 so that aggregates labeled with PKH2 Green dye alternated with aggregates labeled with PKH26 Red dye, in order to better visualize fusion. The resulting structure was incubated at 37° C., and then cooled to room temperature. Aggregate fusion was then detected using confocal microscopy.

After 80 hours of incubation, the final configurations 1603 (agarose gel), 1604 (1.7 mg/ml collagen), and 1605 (1.0 mg/ml collagen) were recorded photographically. The boundaries 1606 of neighboring aggregates and the embedding gel when 1.0 mg/ml collagen is used were also recorded photographically. An enlarged view 1607 (at 60× magnification) of the interior of the contact region between aggregates when 1.0 mg/ml collagen is used was also recorded photographically.

Formation of a Fused Tube Structure

Referring to FIGS. 17A-17I, the fluorescently labeled CHO cell aggregates described above were used to form a three dimensional fused tube structure.

Ten of the fluorescently labeled cell aggregates were contiguously arranged (either manually or printed) to form a closed circle on 1.0 mg/ml collagen, as prepared in Example 2. A second ring layer, again comprising 10 fluorescently labeled cell aggregates contiguously arranged to form a closed circle (manually or by printing using a 3D bioprinter) on the 1.0 mg/ml collagen gel, was closely stacked in the vertical direction on the first ring layer. This process was repeated until a structure comprising three layers of vertically stacked rings was produced, each layer comprising cell aggregates fluorescently labeled with a different color dye (e.g., PKH2 Green or PKH26 Red). The resulting structure was incubated at 37° C. and cooled to room temperature, as described above. Aggregate fusion was then detected using confocal microscopy.

Figures 17A, 17B, 17C:
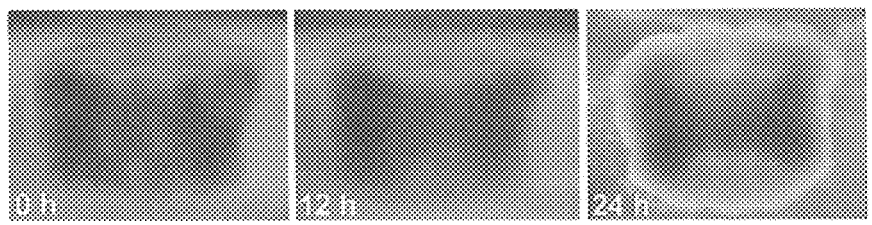
FIGS. 17A-17I is a sequence of fluorescent images showing tube structure formation over time, as described in Example 5.
Figures 17D, 17E, 17F:
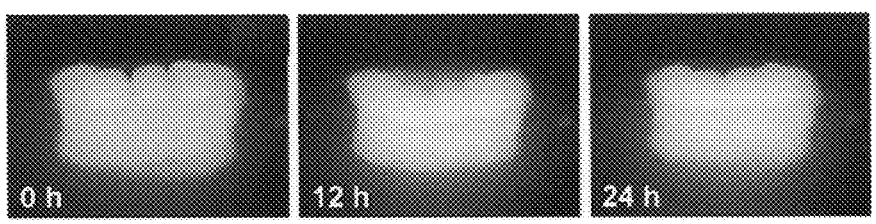
Figures 17G, 17H, 17I:
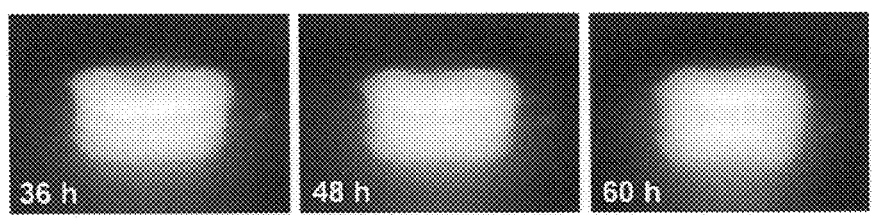
Figure 18:
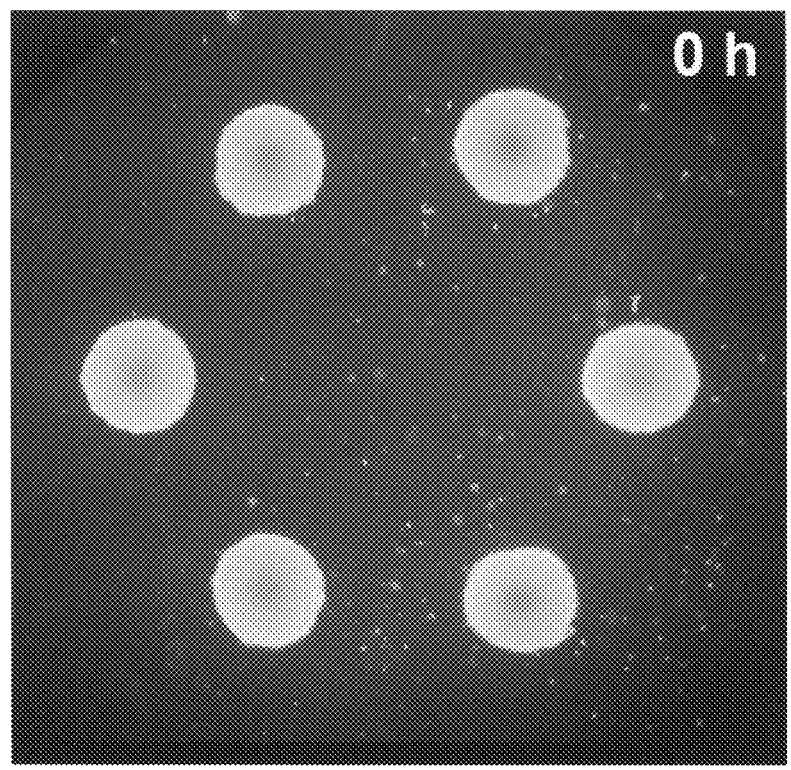
FIG. 18 is an image of CHO cell aggregates of approximately 500 micron diameter, produced as described in Example 1, printed in a hexagon pattern on 1.0 mg/ml collagen.

The resulting structures are shown in FIGS. 17A-17I. FIGS. 17A-17C are bright field images of pattern evolution of three vertically closely packed rings towards a hollow tube at 0 hours (FIG. 17A), 12 hours (FIG. 17B), and 24 hours (FIG. 17C). FIGS. 17D-17I are fluorescent images of this process after 0 hours (FIG. 17D), 12 hours (FIG. 17E), 24 hours (FIG. 17F), 36 hours (FIG. 17G), 48 hours (FIG. 17H), and 60 hours (FIG. 17I).

CONCLUSION

When introducing elements of the present invention or the preferred embodiments thereof, the articles "a", "an", "the", and "said" are intended to mean that there are one or more of the elements. The terms "comprising", "including," and "having" are intended to be inclusive and mean that there may be additional elements other than the listed elements.

In view of the above it will be seen that the several objects of the invention are achieved and other advantageous results attained.

As various changes could be made in the above constructions, compositions, and methods without departing from the scope of the invention, it is intended that all matter contained in the above description and shown in the accompanying drawings shall be interpreted as illustrative and not in a limiting sense.

What is claimed is:

1. A three-dimensional layered structure comprising: at least one layer of a matrix; and a plurality of cell aggregates, each cell aggregate comprising a plurality of living cells; wherein the cell aggregates are embedded in the at least one layer of matrix in a non-random predetermined pattern, the cell aggregates having predetermined positions in the pattern.

2. The structure of claim 1, wherein the cell aggregates are substantially uniform in size and shape.

3. The structure of claim 1, wherein the cell aggregates are cylindrical.

4. The structure of claim 1, wherein the cell aggregates are substantially spherical.

5. The structure of claim 1, wherein each cell aggregate comprises a plurality of living cells of a single cell type.

6. The structure of claim 1, wherein at least one of the cell aggregates comprises a plurality of living cells of a first type and a plurality of living cells of a second type, the second type being different from the first type.

7. The structure of claim 1, wherein the plurality of cell aggregates includes at least one cell aggregate consisting essentially of cells of a first type and at least one other cell aggregate consisting essentially of cells of a second type, the second type being different from the first type.

8. The structure of claim 1, wherein the at least one layer of matrix is biocompatible and about 100 microns to about 600 microns thick.

9. The structure of claim 1, wherein the at least one layer of matrix is biocompatible and selected from the group consisting of thermo-reversible gels, photo-sensitive gels, pH-sensitive gels, cell type specific gels, and combinations thereof.

10. The structure of claim 1, wherein the at least one layer of matrix is biocompatible and comprises at least two different types of biocompatible matrices.

11. The structure of claim 1, comprising: a first layer of matrix; and a second layer of matrix deposited on the first layer; wherein the first layer and second layer of matrix are biocompatible; wherein the cell aggregates are embedded in the first layer and in the second layer in a predetermined pattern.

12. The structure of claim 3, wherein the cylindrical cell aggregates are from about 100 microns to about 600 microns in cross-sectional diameter.

13. The structure of claim 4, wherein the substantially spherical cell aggregates are between about 100 and about 600 microns in diameter.

14. The structure of claim 11, further comprising at least one additional layer of matrix deposited on the second layer, wherein the at least one additional layer of matrix is biocompatible, wherein the cell aggregates are embedded in the first layer, the second layer, and the at least one additional layer in a predetermined pattern.

15. The structure of claim 11, wherein the first layer comprises a type of biocompatible matrix that is different from the type of biocompatible matrix in the second layer.

16. The structure of claim 6, wherein the cells of the first type are smooth muscle cells and the cells of the second type are endothelial cells.

17. The structure of claim 7, wherein the cells of the first type are smooth muscle cells and the cells of the second type are endothelial cells.

18. A method of producing a plurality of fused aggregates forming a desired three-dimensional structure, the method comprising: depositing a layer of a matrix on a substrate; embedding a plurality of cell aggregates, each comprising a plurality of cells, in the layer of the matrix to form a three-dimensional layered structure of claim 1, the aggregates being arranged in a non-random predetermined pattern, wherein the cell aggregates have predetermined positions in the pattern; allowing at least one aggregate of said plurality of cell aggregates to fuse with at least one other aggregate of the plurality of cell aggregates to form the desired structure; and separating the structure from the matrix.

19. The method of claim 18, wherein the layer of the matrix constitutes a first layer, the plurality of cell aggregates constitutes a first plurality of cell aggregates, and the predetermined pattern constitutes a first predetermined pattern, the method further comprising the steps of: depositing a second layer of the matrix on the first layer; and embedding a second plurality of cell aggregates in the second layer, the second plurality of cell aggregates comprising a plurality of cells, the second plurality of cell aggregates being arranged in a second predetermined pattern, and allowing at least one cell aggregate in the first plurality of cell aggregates to fuse with at least one cell aggregate in the second plurality of cell aggregates.

20. The method of claim 18, wherein the thickness of the layer of the matrix is about equal to the average diameter of the plurality of cell aggregates.

21. The method of claim 18, wherein the cell aggregates are substantially spherical.

22. The method of claim 18, wherein the cell aggregates are substantially uniform in size.

23. The method of claim 18, wherein the cell aggregates have an average size between about 100 and about 600 microns.

24. The method of claim 18, wherein the cell aggregates consist essentially of cells of a single type.

25. The method of claim 18, wherein at least one of the cell aggregates comprises a plurality of living cells of a first type and a plurality of living cells of a second type that is different from the first type.

26. The method of claim 18, wherein the predetermined pattern comprises a ring.

27. The method of claim 18, wherein the matrix comprises a gel.

28. The method of claim 18, wherein said plurality of cell aggregates includes at least one cell aggregate consisting essentially of cells of a first type and at least one other cell aggregate consisting essentially of cells of a second type different from the first type.

29. The method of claim 19, wherein the first and second predetermined patterns are substantially the same, and wherein the second plurality of cell aggregates is embedded in the second layer of the matrix in registration with the first plurality of cell aggregates.

30. The method of claim 19, wherein the desired structure is a tube, the first and second predetermined patterns are both circular in shape, and the second plurality of cell aggregates is embedded in the second layer of the matrix in registration with the first plurality of cell aggregates.

31. The method of claim 23, wherein no more than about 10% percent of the cell aggregates deviate from said average size by more than 5%.

32. The method of claim 25, wherein said at least one cell aggregate comprises a mixture of said cells of the first type and said cells of the second type and the method further comprises the step of allowing at least some of the cells of the first type to segregate from at least some of the cells of the second type.

33. The method of claim 25, wherein the cells of the first type are epithelial cells and the cells of the second type are connective tissue-forming cells.

34. The method of claim 25, wherein the cells of the first type are smooth muscle cells and the cells of the second type are endothelial cells.

35. The method of claim 28, wherein the cells of the first type are smooth muscle cells and the cells of the second type are endothelial cells.

* * * * *

UNITED STATES PATENT AND TRADEMARK OFFICE
CERTIFICATE OF CORRECTION

| | | |
|---|---|---|
| PATENT NO. | : 8,241,905 B2 | Page 1 of 1 |
| APPLICATION NO. | : 10/590446 | |
| DATED | : August 14, 2012 | |
| INVENTOR(S) | : Forgacs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,212 days.

Signed and Sealed this
Twenty-ninth Day of January, 2013

David J. Kappos
*Director of the United States Patent and Trademark Office*